US007574007B2

(12) United States Patent
Shaw et al.

(10) Patent No.: US 7,574,007 B2
(45) Date of Patent: **\*Aug. 11, 2009**

(54) STIMULUS ANALYSIS SYSTEM AND METHOD HAVING ADAPTIVE ARTIFACT REJECTION

(75) Inventors: Gregory R. Shaw, Calgary (CA); Mead C. Killion, Elk Grove Village, IL (US)

(73) Assignee: Etymotic Research, Inc., Elk Grove Village, IL (US)

( * ) Notice: Subject to any disclaimer, the term of this patent is extended or adjusted under 35 U.S.C. 154(b) by 1779 days.

This patent is subject to a terminal disclaimer.

(21) Appl. No.: 10/035,455

(22) Filed: Nov. 1, 2001

(65) Prior Publication Data

US 2002/0099306 A1  Jul. 25, 2002

Related U.S. Application Data

(63) Continuation of application No. 09/528,055, filed on Mar. 17, 2000, now Pat. No. 6,331,164.

(51) Int. Cl.
*H04B 15/00* (2006.01)

(52) U.S. Cl. .................. 381/94.7; 381/58; 381/71.1; 600/559; 73/585; 342/165

(58) Field of Classification Search ............... 381/94.7, 381/94.1, 94.2, 160, 158, 71.1, 71.6, 60, 381/58, 94.3, 71.2; 600/559, 300; 73/585; 342/165

See application file for complete search history.

(56) References Cited

U.S. PATENT DOCUMENTS 5,601,091 A * 2/1997 Dolphin ................... 600/559
6,198,693 B1 * 3/2001 Marash ..................... 367/125

OTHER PUBLICATIONS

J. G. Proakis and D. G. Manolakis, Digital Signal Processing, Third Edition, Printice-Hall, New Jersey, 1996, pp. 448-475.*

* cited by examiner

*Primary Examiner*—Vivian Chin
*Assistant Examiner*—Con P Tran
(74) *Attorney, Agent, or Firm*—McAndrews, Held & Malloy, Ltd.

(57) ABSTRACT

A stimulus analysis system and artifact rejection method are disclosed. The method may be used in many applications, such as, for example, DPOAE testing, TEOAE testing, BAER testing, ultrasound, MRI, RADAR, GPS, EEG, EKG, or communications. In one embodiment, a system receives a signal, and depending on the noise power of the signal, the signal is placed in one of a plurality of buffers or is discarded. This process is repeated. The combination of buffers that yields the lowest noise power is then selected. The selected combination of buffers may then be used to calculate a signal to noise ratio, which may be used to determine whether the signal received is acceptable, indicating, for example, that a test has been passed or failed.

18 Claims, 19 Drawing Sheets

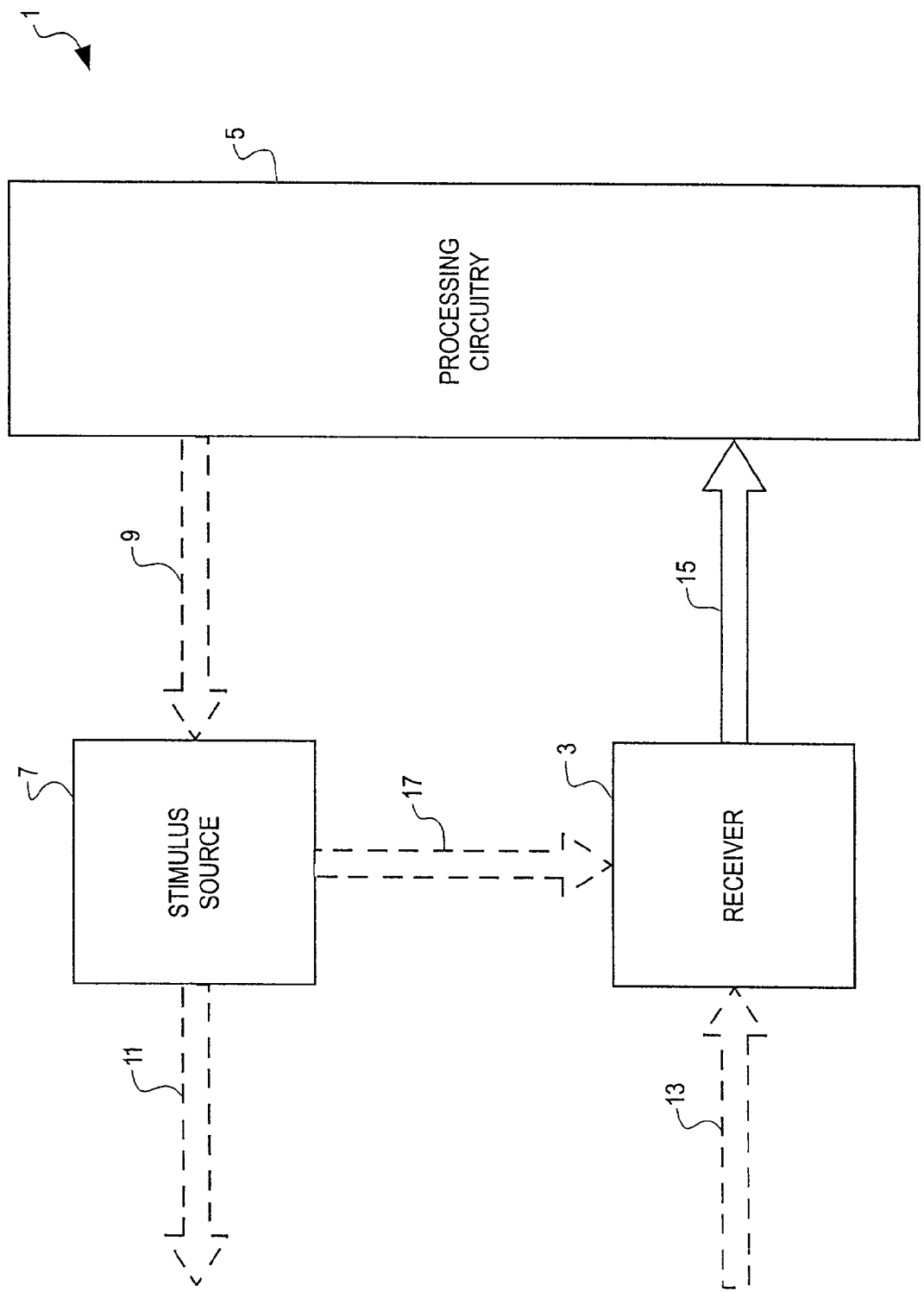

STIMULUS ANALYSIS SYSTEM AND METHOD HAVING ADAPTIVE ARTIFACT REJECTION

CROSS-REFERENCE TO RELATED APPLICATIONS

This application is a continuation of U.S. application Ser. No. 09/528,055 filed Mar. 17, 2000, now U.S. Pat. No. 6,331,164.

INCORPORATION BY REFERENCE

U.S. application Ser. No. 09/528,055 filed Mar. 17, 2000 is hereby incorporated herein by reference in its entirety.

STATEMENT REGARDING FEDERALLY SPONSORED RESEARCH OR DEVELOPMENT

N/A

BACKGROUND OF THE INVENTION

Signal averaging is known, and is often employed in the measurement of experimental signals. More particularly, signal averaging is generally used to measure weak response signals to a repetitive stimulus. Such response signals often have a magnitude that is low relative to an accompanying background noise level, making accurate measurement of such response signals difficult. Signal averaging is used to increase the signal-to-noise ratio of such response signals.

Signal averaging is generally performed by measuring the response signals repeatedly in succession, adding all of the response signals measured, and dividing by the number of repeated measurements. Signal averaging is based on the principle that the background noise is usually uncorrelated from measurement to measurement (i.e., random) and will therefore gradually cancel out, while the desired response signal is repeatable and will therefore continue to add up. Signal averaging, as such, is therefore used to reveal response signals that are buried in the background noise, and would thus be otherwise undetectable.

Many applications currently use signal averaging to improve the signal-to-noise ratio of desired signals. Signal averaging is used in many medical procedures, such as, for example, electrocardiography ("EKG"), electroencephalography ("EEG"), magnetic resonance imaging ("MRI"), brainstem auditory evoked response ("BAER") testing, transient evoked otoacoustic emissions (TEOAE) testing, distortion product otoacoustic emissions ("DPOAE") testing, and ultrasound imaging. Signal averaging is also used in many non-medical applications, such as, for example, ultrasound imaging analysis of various materials and their properties, global positioning systems ("GPS"), radio detecting and ranging ("RADAR"), various types of spectroscopy, and communications.

Most of the above applications are performed in environments having considerable background noise present. For example, medical procedures are performed in rooms having fluorescent light ballasts, power supplies, sensors, heaters, computer equipment, etc., all of which contribute to the background noise. In addition, for applications measuring stimulus-evoked responses, such as, for example, BAER, TEOAE and DPOAE testing, the ongoing background activity of the brain may also contribute to the background noise. In fact, the stimulus itself may produce an artifact that obscures the response signal of interest. Thus, in any given application, the background noise can vary considerably, causing variations in the overall measured magnitude.

One traditional signal averaging approach to combat such problems is to generate a noise floor threshold, reject the values measured above the threshold as noise, and accept those below. In application, this approach involves measuring the response, calculating the noise floor, and then adding the response to an average buffer only if the noise floor is below a threshold value. The number of responses added to the buffer is counted, and only those signals are used in the averaging calculation.

However, an optimal threshold cannot be determined until after the test is completed. A simple approach to generate an optimal threshold, therefore, is to wait until the test is completed. In other words, the data is recorded first, and then used to determine the most optimal noise floor threshold. Such approach, however, requires that the complete response must be stored, making such approach often impractical due to memory and battery limitations. This is particularly true in applications that use hand-held test devices, such as, for example, DPOAE testing, where memory storage is limited and battery drain is a critical operating factor. In addition, such approach is impractical in applications where real-time measurements are desired, particularly in the medical field.

It is therefore an object of the invention to provide an improved and practical signal averaging approach for many applications.

SUMMARY OF INVENTION

Aspects of the invention are found in a stimulus analysis system that receives a signal, and places the signal received into one of a plurality of buffers or discards it, depending on the noise power of the signal. The device then selects the combination of buffers that yields the lowest noise floor estimate. The selected combination of buffers may then be used to analyze the signal.

In one embodiment, the selected combination of buffers is used to calculate a signal to noise ratio, which is then compared to a predetermined value. If the calculated signal to noise ratio is greater than the predetermined value, a first function is performed, for example. If the calculated signal to noise ratio is lower than the predetermined value, a second function is performed, for example.

In another embodiment, the signal received by the system is split into a noise component and a signal component, by, for example, taking the discrete Fourier transform of the signal. The noise component is used to calculate a noise power value, and depending on that value, the noise component is placed within one of a plurality of noise buffers or is discarded. The signal component is then placed in one of a plurality of signal buffers corresponding to the noise buffers, or is discarded, as the case may be. The system then selects the combination of noise buffers yielding the lowest noise power, and calculates the signal power using the same corresponding signal buffers. The noise power and signal power are then used to calculate the signal to noise ratio, which is compared to a predetermined value. Again, if, for example, the calculated signal to noise ratio is greater than the predetermined value, a first function is performed, otherwise, a second function is performed, for example.

The method of the present invention may be used in many applications, such as, for example, DPOAE testing, TEOAE testing, BAER testing, ultrasound, MRI, RADAR, GPS, EEG, EKG, or communications.

These and other advantages and novel features of the present invention, as well as details of an illustrated embodiment thereof, will be more fully understood from the following description and drawings.

BRIEF DESCRIPTION OF THE SEVERAL VIEWS OF THE DRAWING

FIG. 1 illustrates a system for employing the method of the present invention, and shows potential flow of information according to the invention.

DETAILED DESCRIPTION OF THE INVENTION

Figure 2A:
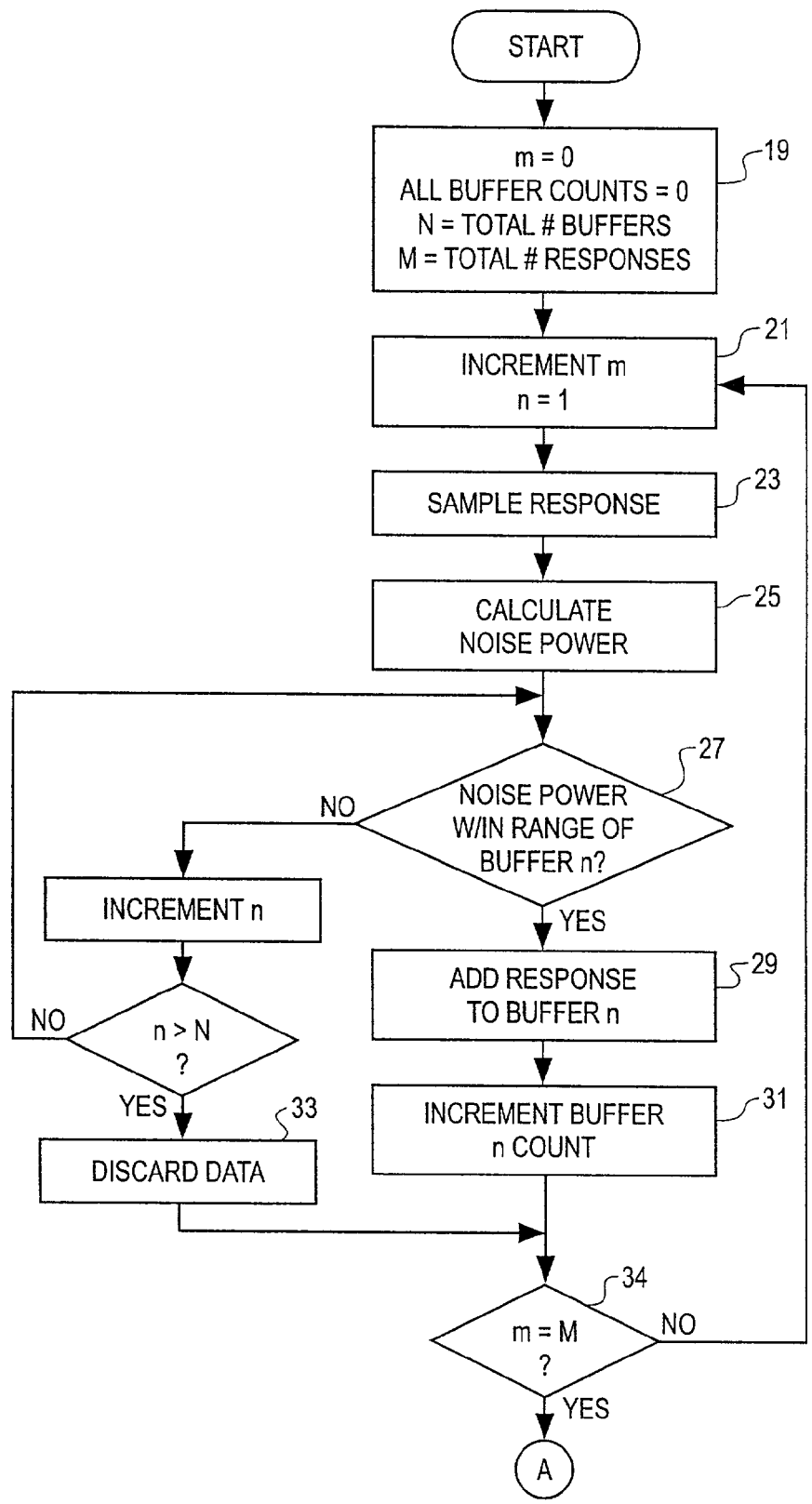
FIG. 2A-2B are a flow diagram illustrating one embodiment of the artifact rejection method of the present invention.

FIG. 1 illustrates a system for employing the method of the present invention, and shows potential flow of information according to the invention. The system 1 generally employs a receiver 3 for receiving response signals, and processing circuitry 5 for processing the response signals. The processing circuitry may comprise, for example, a microprocessor, an analog to digital and digital to analog converter, and associated circuitry. The system also employs a stimulus source 7.

In one embodiment, the processing circuitry 5 generates signals representative of desired stimuli, and transmits the signals to the stimulus source 7 via communication link 9. The stimulus source 7 in turn generates the desired stimuli and transmits the stimuli as represented by arrow 11. The receiver 3 receives signals, as represented by arrow 13, that are responsive to the stimuli, and communicates the response signals to the processing circuitry 5 via communication link 15. This embodiment of the system may be used in various applications, such as, for example, DPOAE testing, TEOAE testing, BAER testing, ultrasound, MRI, RADAR, GPS, EEG, etc.

In an alternative embodiment, the stimulus source 7 is not directly controlled by the processing circuitry 5 via communication link 9. Instead, the stimulus source generates its own signals, represented by arrow 17, that are received by the receiver 3 and communicated to the processing circuitry 5 via communication link 15. This embodiment may be employed in other applications, such as, for example, in EKG recordings.

In another embodiment, the stimulus source 7 is again not directly controlled by the processing circuitry 5 via communication link 9. Instead, the stimulus source 7 may be controlled by other processing circuitry (not shown) and may be at a location remote from the receiver 3 and processing circuitry 5. In this embodiment, the stimulus source 7 generates signals, represented by arrow 17, that are received by the receiver 3 and communicated to the processing circuitry 5. This embodiment of the system may be employed in other applications. such as, for example, communications applications.

In any event, it should be understood that the above embodiments are exemplary only, and that any system or apparatus that benefits or could benefit from signal averaging may employ the method of the present invention.

Figure 2B:
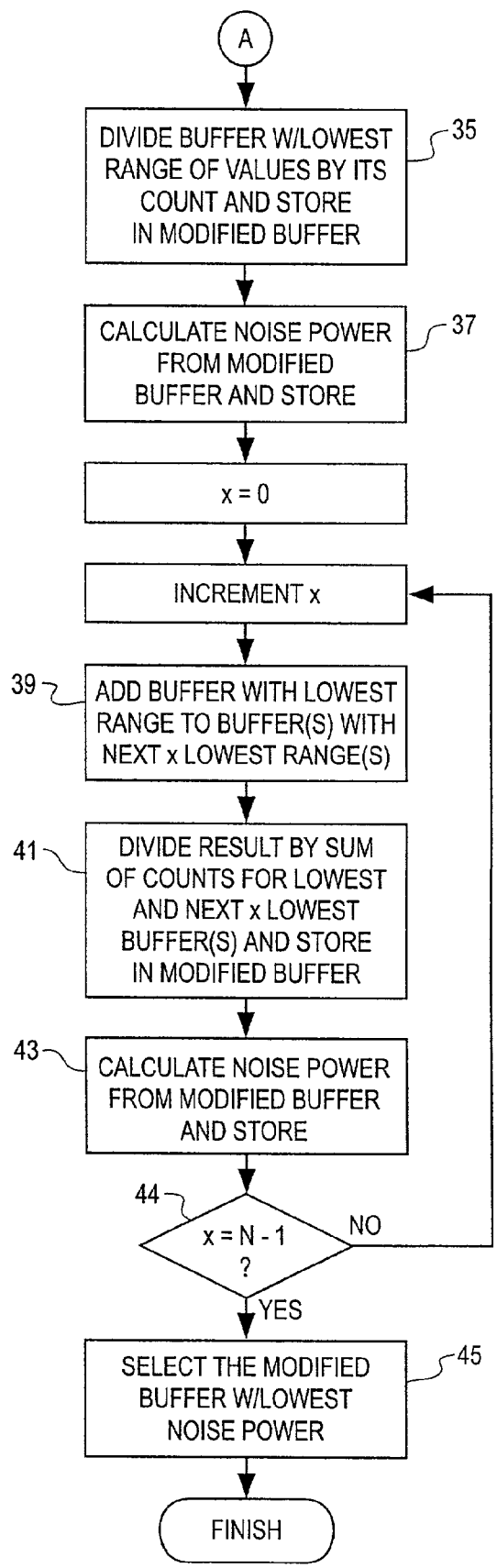

FIGS. 2A and 2B are a flow diagram illustrating one embodiment of the artifact rejection method of the present invention. FIG. 2A may be referred to as a data acquisition phase. The system is initialized by setting a counter variable m and all buffer counts to zero (block 19). The counter variable m is used in a loop to determine if the system has sampled the total number of expected responses, represented by a variable M. The system then increments m and sets another counter variable n equal to the 1 (block 21). The counter variable n is used in a second loop to determine which of a total number of buffers, represented by a variable N, corresponds to the sampled response.

More specifically, the system samples a response (block 23), and calculates the noise power of the response (block 25). Next, the system determines whether the noise power is within a noise power range corresponding to a first buffer (block 27). If it is, the response is added to a first buffer (block 29), and a first buffer count is incremented (block 31). The system then loops back to sample another response.

If the noise power of the response is not within range of the first buffer, the system loops to block 27 to determine whether the response is within a noise power range of a second buffer. Again, if it is, the response is added to the second buffer (block 29), the second buffer count is incremented (block 31) and the system loops back to sample another response. If the response is not within range of the second buffer, then the third buffer is tried, and so on. This loop is repeated for each of the total number of buffers N. If the response is not within a noise power range of any of the buffers, then the data is discarded (block 33). This whole process is repeated until the total number of responses M has been sampled.

In other words, each response is sampled, and depending on the calculated noise power, is placed within one of a plurality of buffers or is discarded. This is repeated for a plurality of responses, and the system keeps track of the number of responses placed in each respective buffer. Once the total number of responses have been sampled (i.e., m=M at block 34), the data acquisition phase is complete.

The system next advances to FIG. 2B, which may be referred to as a data analysis phase. The system first divides the buffer having the lowest range of values by the number of samples that were placed in that buffer and stores the result (block 35). The result is then used to calculate the noise power, which is stored in a buffer (block 37).

The system next adds the buffer having the lowest range of values to the buffer having the next lowest range of values (block 39), and then divides the result by the total number of responses that were placed in both of those buffers (block 41) and stores the result. This result is then used to calculate the noise power, which is stored in a buffer (block 43). Similarly, the system next adds the buffer having the lowest range of values to the buffers having the next two lowest ranges of values (block 39) and then divides the result by the total number of responses that were placed in those three buffers (block 41) and stores the result. This result is then used to calculate the noise power, which is likewise stored in a buffer (block 43).

This process is repeated for the total number of buffers (i.e., until x=N−1 at block 44), so that the system has N estimates of the noise power. The system then selects the estimate (i.e., normalized combination of buffers) with the lowest value (block 45). The selected combination of buffers represents the quietest portion of data, and is used by the system for further analysis, depending on the application. In other words, the system has determined a subset of responses that, when averaged together, result in the lowest overall noise floor.

FIGS. 3A-3D are a more detailed flow diagram of one embodiment of the artifact rejection method of the present invention. The following are variable definitions used in conjunction with FIGS. 3A-3D:

Stimulus output to system (vector-size N)
X=response from system (vector-size N)
S=signal sum buffers (matrix-size N by M)
Count=buffer count (vector-size M)
T=threshold values (vector-size M)
monotonically increasing values
Ssum=cumulative sum buffers (matrix-size N by M)
CountSum=cumulative sum count (vector-size M)
NF=noise floor est. based on 1st m sum buffers (vector-size M)
W=penalty weighting function (vector-size M)
application specific
AveragedResponse=final signal estimate (vector-size N)
M=number of buffers
N=size of time averaged response
blocks=stimulus count
blocks_max=total number of stimulus presented by system
nf=noise floor of the current noise component The system is initialized by setting the variables S, blocks and Count equal to zero (block 51). Next, a Stimulus is applied by the system (block 53), and a response X is received by the system in response to the stimulus (block 55). Both the Stimulus and response X are vectors of size N. The response X is then used by the system to calculate a noise floor estimate, nf (block 57).

The calculation of the noise floor estimate, nf, is application specific, and may employ a number of different methods. For example, a double response method may be used. In the double response method, two sequential responses are obtained by the system, are subtracted, and then divided by 2. The resulting values are an estimate of the noise. The resulting values are then squared and added to obtain the noise floor estimate. The following example illustrates a calculation using one embodiment of the double response method:

$$A = \begin{bmatrix} 7 \\ 2 \\ 3 \end{bmatrix} B = \begin{bmatrix} 7 \\ 1 \\ -2 \end{bmatrix}$$

$$noise = \left(\frac{A-B}{2}\right) = \begin{bmatrix} 0 \\ 0.5 \\ 2.5 \end{bmatrix}$$

$$nf = (0)^2 + (0.5)^2 + (2.5)^2$$
$$= 0 + .25 + 6.25$$
$$= 6.50$$

Another method that may be used is the time division method. In this method, the system considers a portion of the response in time generally where a low response is expected, squares each value, and then adds them.

A further method that may be employed is the frequency division method. In this method, the response is decomposed in frequency by taking the Fast Fourier Transform (FFT) of the response or by using a bandpass filter. If a bandpass filter is used, each value (or a portion thereof) is then added to obtain the noise floor estimate. If the FFT is taken, the absolute value of each complex number (or a portion thereof) is squared and then added. The following example illustrates one embodiment of the frequency division method employing an FFT:

$$x = \begin{bmatrix} 1 \\ 2 \\ -1 \\ 0 \\ 1 \\ 3 \\ 2 \\ -1 \end{bmatrix} FFT(x) = \begin{bmatrix} -7.0 \\ -\sqrt{2} - 3i \\ 1.0 + 6i \\ \sqrt{2} + 3i \\ -1.0 \\ \sqrt{2} - 3i \\ 1.0 - 6i \\ -\sqrt{2} + 3i \end{bmatrix}$$

$$nf = |1 + 6i|^2 + |\sqrt{2} + 3i|^2$$
$$= 37 + 11 = 48$$

In general, the above methods for calculating the noise floor estimate may be combined, depending upon the desired application.

Referring again to FIGS. 3A-3D, once the noise floor estimate is obtained from the response, the system determines whether the noise floor estimate is less than a lowest threshold value T(1) of a vector T (block 59). As mentioned above, the vector T has values that are monotonically increasing. In other words each value is successively larger (i.e., T is sorted). Thus T(2) is greater than T(1), but is less than the rest of the values of T. Similarly, T(3) is greater than T(1) and T(2), but less than the rest of the values of T, and so on.

The lowest threshold value T(1) is predetermined, application specific, and constitutes the lowest expected noise floor. T(1) may be determined by calculating nf a selected number of times under quiet conditions (e.g., 100), calculating the mean and standard deviation of nf, and then setting T(1) equal to the mean plus three standard deviations. In any event, T(1) is chosen such that a large percentage of the noise floor estimates are less than T(1) under quiet conditions (e.g., greater than 99% are less than T(1)).

If the noise floor estimate is less than T(1), the first position in the Count vector is incremented (block 61), and the response corresponding to the noise floor estimate is added to the first signal sum buffers matrix S (block 63). Next, the blocks counter is incremented (block 65) and, assuming that the total number of stimuli have not been presented by the system (block 67), the system applies another stimulus (block 53).

If the noise floor estimate is not less than T(1), the system enters a loop, limited by the number of buffers N to determine whether the value of nf falls between two successive values in T (block 69). In other words, the system loops to determine in which buffer (i.e., column in matrix S) the noise floor estimate belongs. If the nf value falls within an appropriate range of T, the Count vector is incremented (block 61), keeping track of how many times each respective nf falls within that range, and the associated response is added to the appropriate column in matrix S.

If the nf value does not fall within an appropriate range of T, the response is discarded.

In any event, the system continues the above process until the total number of stimuli have been applied (block 67).

When the total number of stimuli have been applied (i.e., when blocks>blocks_max), the data acquisition phase is complete. At this point, the data has been sorted and resides in appropriate buffers.

Figure 3A:
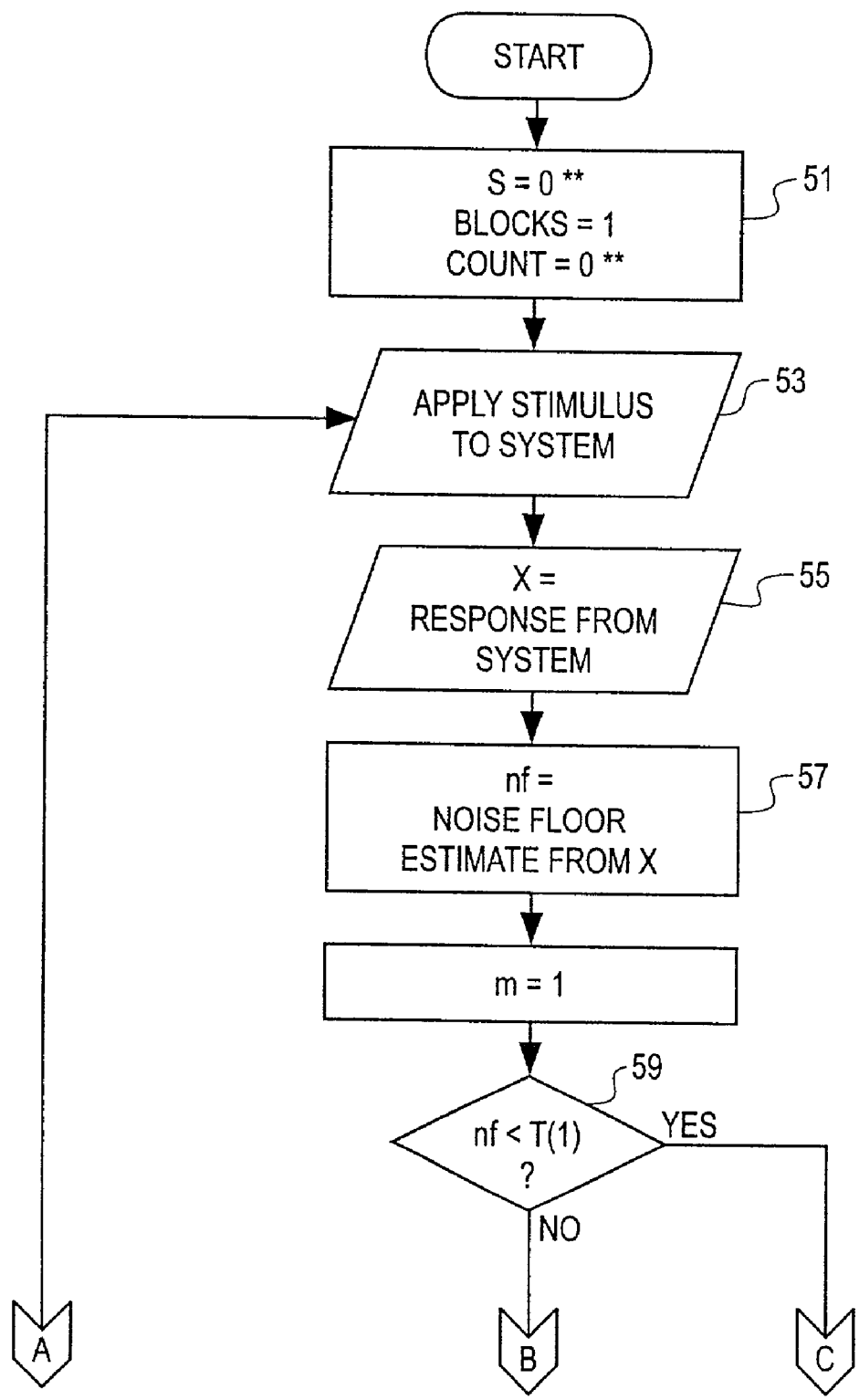
FIGS. 3A-3D are a more detailed flow diagram of one embodiment of the artifact rejection method of the present invention.
Figure 3B:
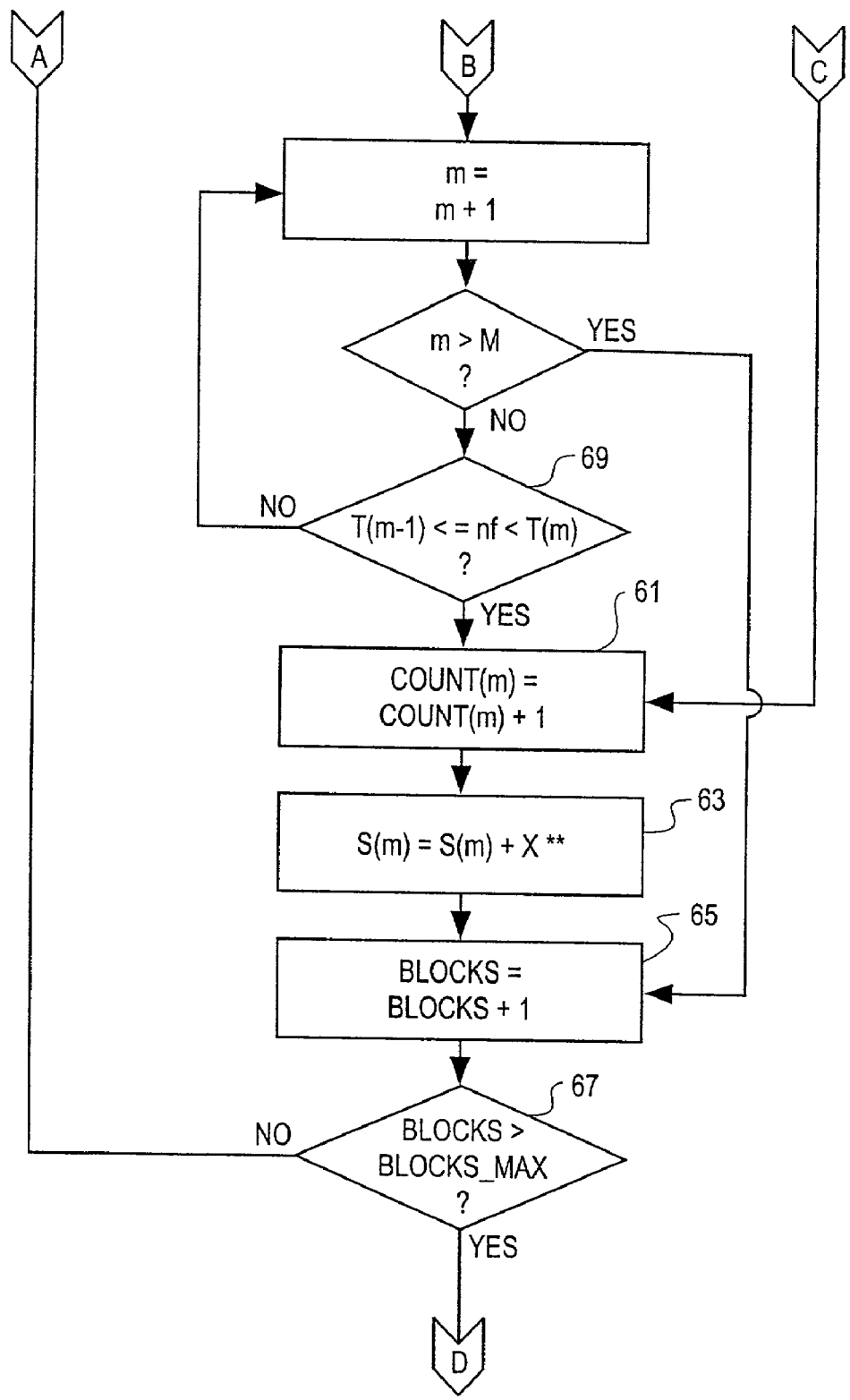
Figure 3C:
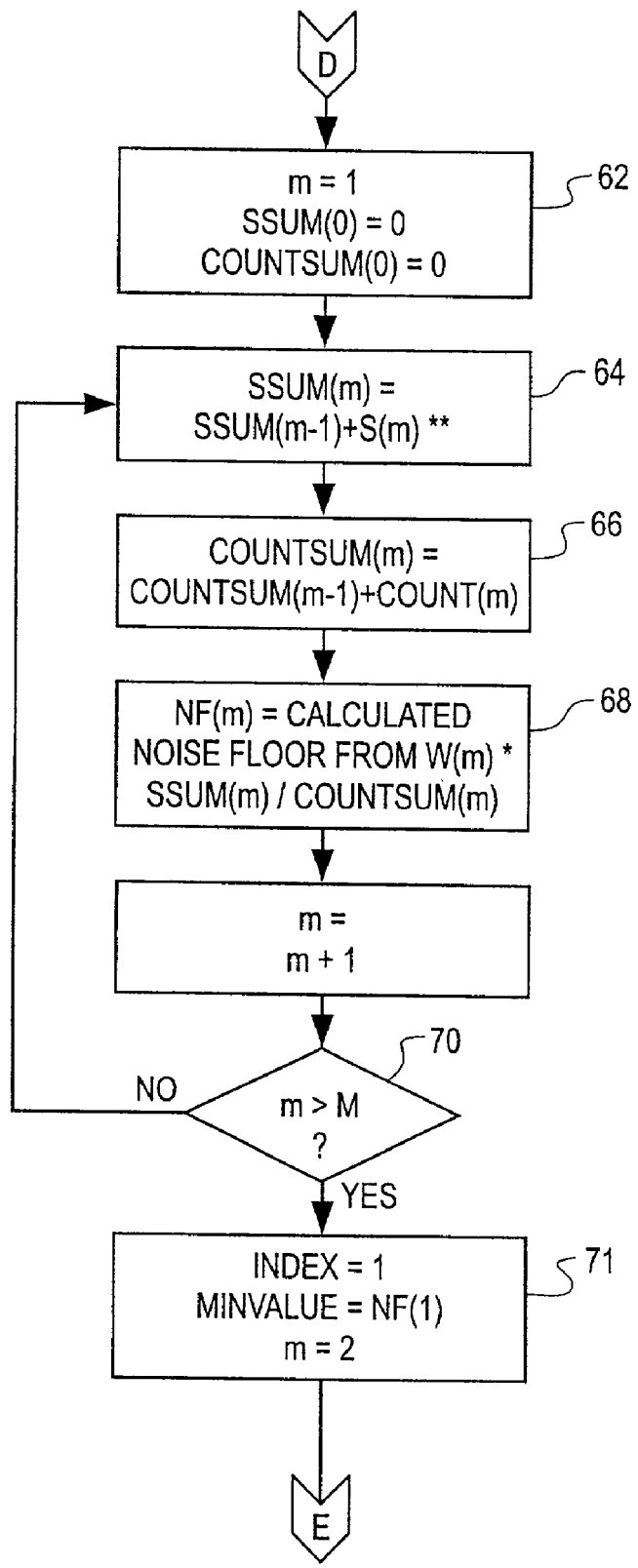
Figure 3D:
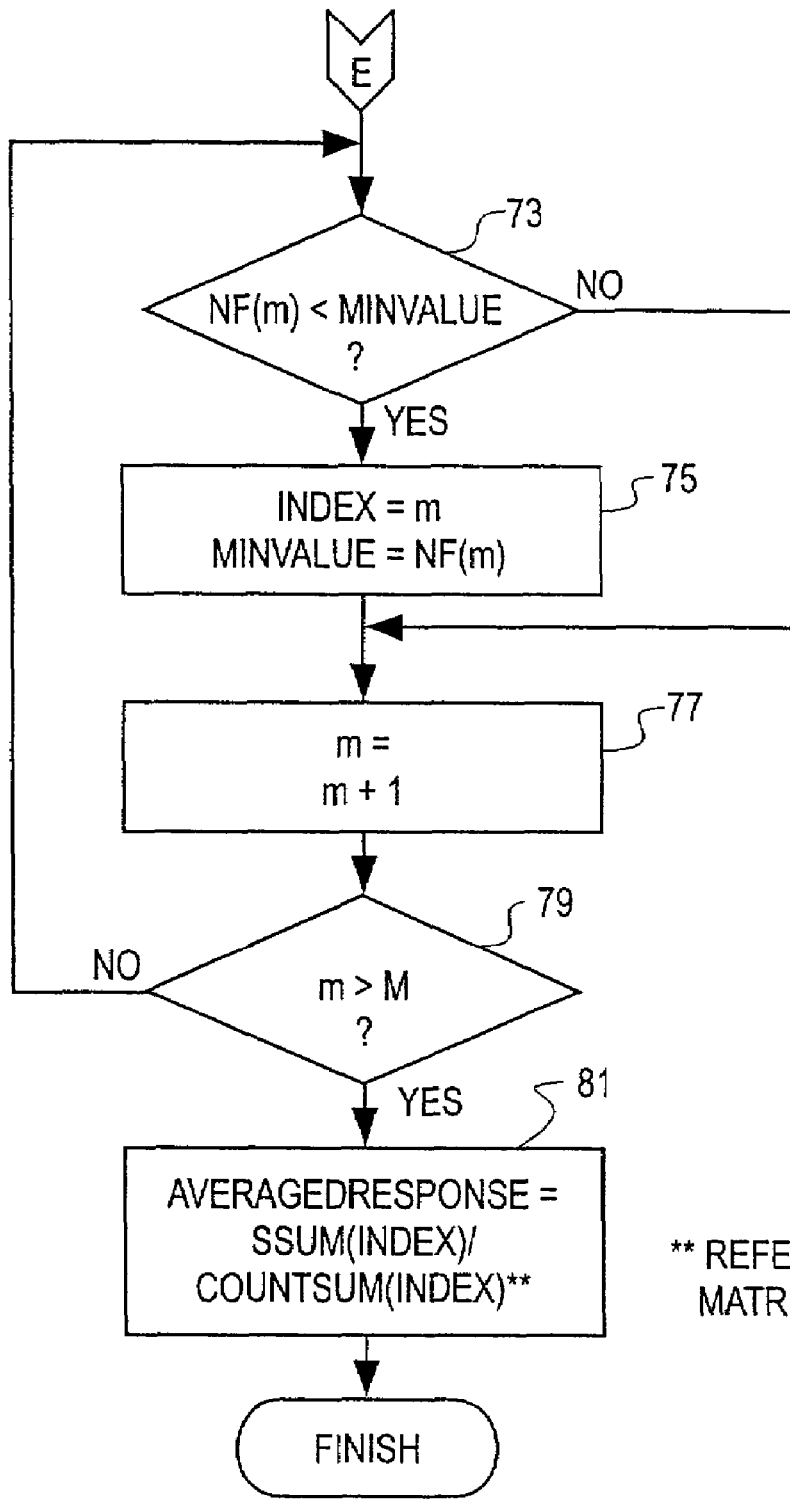

FIG. 3C begins the data analysis or processing phase. The phase is initialized by setting the loop variable m equal to 1, the cumulative sum buffers matrix to zero, and the cumulative sum count vector to zero (block 62). The system next enters a loop to generate M calculations of the noise floor estimate based on the signal sum buffers. Generally, this is achieved by generating a cumulative sum matrix (Ssum) and a cumulative sum count vector (CountSum) (blocks 64 and 66, respectively), dividing Ssum by CountSum (block 68), multiplying by a penalty weighting function W, and then repeating for all M buffers.

More specifically, in a first loop, $Ssum_1$ is determined to be equal to $S_1$, CountSum(1) is determined to be equal to Count(1), and NF(1) is calculated from $S_1$ multiplied by W(1) and divided by Count(1). The method of calculating NF(1) is application specific. W is a penalty weighting function, and is used because the system may underestimate the true noise floor. The penalty weighting function is designed to force the system to accept more data than it otherwise would under non-weighted conditions. Of course, there are ways other than as disclosed herein to implement a penalty weighting function. It should be understood that such ways are included within the scope of the present invention.

As explained above, $S_1$ represents all the responses having a noise floor (nf) determined to be less than T(1), and Count(1) equals the total number of such responses. In other words, the noise floor estimate NF(1) is calculated by dividing the buffer with the lowest range of values by the number of values in that buffer, and then multiplying by a penalty weighting function.

Next, in a second loop, $Ssum_2$ is calculated as $Ssum_1+S_2$, CountSum(2) is calculated as CountSum(1)+Count(2), and the noise floor estimate is calculated from $Ssum_2$ multiplied by W(2) and divided by CountSsum(2). As explained above, $S_2$ represents all the responses having a noise floor (nf) that are not less than T(1), but are less than T(2). In other words, the noise floor estimate NF(2) is calculated from the sum of the buffers with the lowest and second lowest range of values divided by the total number of responses placed in both those buffers, and then multiplying by a penalty weighting function.

In a third loop, $Ssum_3$ is calculated as $Ssum_2+S_3$, CountSum(3) is calculated as CountSum(2)+Count(3), and NF(3) is calculated as $Ssum_3$ multiplied by W(3) and divided by CountSum(3). As explained above, $S_3$ represents all of the responses having a noise floor (nf) that are not less than T(2), but are less than T(3). In other words, the noise floor NF(3) is calculated from the sum of the buffer with the lowest range of values and the second and third lowest ranges of values divided by the total number of responses placed in those three buffers, and then multiplying by a penalty weighting function.

The above is repeated until the loop variable m is greater than M (block 70), indicating that all of the buffers have been considered and that M noise floor estimate (NF) vectors have resulted.

The system next enters a loop to determine which NF is the smallest. The loop is initialized by setting an index variable equal to 1, a minvalue variable equal to NF(1) and a loop variable m equal to 2 (block 71). Next, NF(2) is compared to minvalue (i.e., NF(1)) (block 73). If NF(2) is lower, then the index is set at 2 and minvalue is set to equal NF(2) (block 75). If it is not lower, then the index remains at 1 and minvalue remains as NF(1). In either case the loop variable m is incremented (block 77), and the loop repeats until all M buffers have been considered (block 79).

In other words, NF(1) is compared to NF(2), and the smaller is chosen. The smaller of NF(1) and NF(2) is then compared to NF(3) and the smaller is chosen. The smallest of NF(1), NF(2) and NF(3) is then compared to NF(4), and the smaller is chosen, and so on for all M noise floor (NF) buffers. Each time a lower NF is found, the index, which is basically a pointer to a NF vector position, and the minvalue are modified. When all estimates have been considered, the final index indicates which position contains the lowest NF (i.e., minvalue).

Once the index is determined, the AveragedResponse is calculated by dividing the cumulative sum matrix column having the lowest NF (as referenced by the index) by the cumulative sum count for that matrix column (block 81). The resulting value is the final estimate of the signal.

The following is a sample calculation of the AveragedResponse based on the flow diagram of FIGS. 3A-3D. First, assume that there are four responses total (i.e., blocks_max=4) as follows:

$$x_1 = \begin{bmatrix} 5 \\ 3 \\ -2 \\ 6 \\ 8 \\ 1 \end{bmatrix} \quad x_2 = \begin{bmatrix} -5 \\ 1 \\ -2 \\ 4 \\ 1 \\ -3 \end{bmatrix} \quad x_3 = \begin{bmatrix} 2 \\ -2 \\ 1 \\ -1 \\ 5 \\ -3 \end{bmatrix} \quad x_4 = \begin{bmatrix} 6 \\ 3 \\ -1 \\ 5 \\ 3 \\ 2 \end{bmatrix}$$

with each response having six components. Next, assume that the noise floor, nf, is calculated using the fifth and sixth components of the response using the sum of the squares method, giving the following equation:

$$nf_j = x_j^2(5) + x_j^2(6)$$

Next, assume that M=3 (i.e., three buffers) and that T(1), T(2) and T(3) are predetermined to be equal to 15, 20 and 40, respectively.

For the first response, the noise floor is calculated as follows:

$$nf_1 = x_1^2(5) + x_1^2(6)$$
$$= (8)^2 + (1)^2$$
$$= 65$$

The system then loops to determine whether nf, is within any range of T. Since $nf_1$ is greater than T(3), the response $x_1$ is discarded, the system increments blocks to 1 (indicating the first response has been processed), and then loops to apply a second stimulus.

For the second response, the noise floor is calculated as follows:

$$nf_2 = x_2^2(5) + x_2^2(6)$$
$$= (1)^2 + (-3)^2$$
$$= 10$$

The system then loops to determine whether $nf_2$ is within any range of T. Since $nf_2$ is less than $T(1)$, the count for the first buffer (m=1) is incremented as follows:

$$Count(1) = Count(1) + 1$$
$$= 0 + 1$$
$$= 1$$

The response $x_2$ is also added to the first column of S as follows:

$$S_1 = S_1 + x_2$$

$$= 0 + \begin{bmatrix} -5 \\ 1 \\ -2 \\ 4 \\ 1 \\ -3 \end{bmatrix} +$$

$$= \begin{bmatrix} -5 \\ 1 \\ -2 \\ 4 \\ 1 \\ -3 \end{bmatrix}$$

The system next increments blocks to 2, indicating that the second response has been processed, and then loops to apply a third stimulus.

For the third response, the noise floor is calculated as follows:

$$nf_3 = x_3^2(5) + x_3^2(6)$$
$$= (5)^2 + (-3)^2$$
$$= 25 + 9$$
$$= 34$$

The system then loops to determine whether $nf_3$ is within any range of T. Since $nf_3$ is between $T(2)$ and $T(3)$, the count for the third buffer (m=3) is incremented as follows:

$$Count(3) = Count(3) + 1$$
$$= 0 + 1$$
$$= 1$$

The response $x_3$ is also added to the third column of S as follows:

$$S_3 = S_3 + x_3$$

$$= 0 + \begin{bmatrix} 2 \\ -2 \\ 1 \\ -1 \\ 5 \\ -3 \end{bmatrix}$$

-continued $$= \begin{bmatrix} 2 \\ -2 \\ 1 \\ -1 \\ 5 \\ -3 \end{bmatrix}$$

The system next increments blocks to 3, indicating that the third response has been processed, and then loops to apply a fourth stimulus.

For the fourth response, the noise floor is calculated as follows:

$$nf_4 = x_4^2(5) + x_4^2(6)$$
$$= (3)^2 + (2)^2$$
$$= 9 + 4$$
$$= 13$$

Again, the determine whether $nf_4$ is within any range of T. Since $nf_4$ is less than $T(1)$, the count for the first buffer (m=1) is incremented as follows:

$$Count(1) = Count(1) + 1$$
$$= 1 + 1$$
$$= 2$$

The response $x_4$ is also added to the first column of S as follows:

$$S_1 = S_1 + x_4$$

$$= \begin{bmatrix} -5 \\ 1 \\ -2 \\ 4 \\ 1 \\ -3 \end{bmatrix} + \begin{bmatrix} 6 \\ 3 \\ -1 \\ 5 \\ 3 \\ 2 \end{bmatrix}$$

$$= \begin{bmatrix} 1 \\ 4 \\ -3 \\ 9 \\ 4 \\ -1 \end{bmatrix}$$

The system next increment blocks, indicating that the fourth response has been processed. Since blocks is now greater than blocks_max (5>4), the data acquisition completed, with the following S matrix and Count vector:

$$S = \begin{bmatrix} 1 & 0 & 2 \\ 4 & 0 & -2 \\ -3 & 0 & 1 \\ 9 & 0 & -1 \\ 4 & 0 & 5 \\ -1 & 0 & -3 \end{bmatrix}$$

$$Count = \begin{bmatrix} 2 & 0 & 1 \end{bmatrix}$$

The system next generates M estimates of the noise floor, using the Ssum matrix, CountSum vector, and the weighting function W. Specifically, assume that W is as follows:

$$W = \begin{bmatrix} 2 & 2 & 1 \end{bmatrix}$$

First, the column of the Ssum matrix is calculated as follows:

$$Ssum_1 = Ssum_0 + S_1$$

$$= 0 + \begin{bmatrix} 1 \\ 4 \\ -3 \\ 9 \\ 4 \\ -1 \end{bmatrix}$$

$$= \begin{bmatrix} 1 \\ 4 \\ -3 \\ 9 \\ 4 \\ -1 \end{bmatrix}$$

The first CountSum position is next calculated as follows:

$$CountSum(1) = CountSum(0) + Count(1)$$

$$= 0 + 2$$

$$= 2$$

The noise floor estimate, NF, is then calculated using the sum of the squares method and the fifth and sixth elements of Ssum as follows:

$$NF(1) = W(1) * [Ssum_1^2(5) + Ssum_1^2(6)] / CountSum(1)$$

$$= W(1)((4)^2 + (1)^2)/2$$

$$= (2)(17)/2$$

$$= 17$$

The system then determines that only the first buffer has been considered (i.e., m≦M), and loops to calculate the second column of Ssum as follows:

$$Ssum_2 = Ssum_1 + S_2$$

$$= \begin{bmatrix} 1 \\ 4 \\ -3 \\ 9 \\ 4 \\ -1 \end{bmatrix} + 0$$

The second CountSum vector position is next calculated as follows:

$$CountSum(2) = CountSum(1) + CountSum(2)$$

$$= 2 + 0$$

$$= 2$$

The noise floor estimate, NF, is then calculated as follows:

$$NF(2) = W(2) * [Ssum_2^2(5) + Ssum_2^2(6)] / CountSum(2)$$

$$= (2)((4)^2 + (-1)^2)/2$$

$$= 17$$

The system then determines that only the first and second buffers have been considered (i.e., m≦M), and loops to calculate the third column of Ssum as follows:

$$Ssum_3 = Ssum_2 + S_3$$

$$= \begin{bmatrix} 1 \\ 4 \\ -3 \\ 9 \\ 4 \\ -1 \end{bmatrix} + \begin{bmatrix} 2 \\ -2 \\ 1 \\ -1 \\ 5 \\ -3 \end{bmatrix}$$

$$= \begin{bmatrix} 3 \\ 2 \\ -2 \\ 8 \\ 9 \\ -4 \end{bmatrix}$$

The third position in the CountSum vector is next calculated as follows:

$$CountSum(3) = CountSum(2) + Count(3)$$

$$= 2 + 1$$

$$= 3$$

The noise floor estimate, NF, is then calculated as follows:

$$NF(3) = W(3) * [Ssum_3^2(5) + Ssum_3^2(6)] / CountSum(3)$$

$$= (1)((9)^2 + (-4)^2)/3$$

$$= 97/3$$

$$= 32.3$$

The system then determines that all three buffers have been considered (i.e., m>M), and the resulting NF vector reads as follows:

$$NF = [17 \ 17 \ 32.3]$$

The system next loops to determine which NF value is the lowest. Specifically, the system initially sets the index to the first position of the NF vector, and minvalue equal to the corresponding NF (i.e., NF(1)). The system then compares NF(2) to determine whether it is less than NF(1). Since 17 is not less than 17, index still points to the first position in NF, and NF(1) remains as minvalue. Next, the system compares NF(3) to (NF(1), and since 32.3 is not less than 17, index still points to the first position of NF, and NF(1) remains as minvalue.

At this point, all NF values have been considered (i.e., m>M) and the AveragedResponse is calculated as follows:

$$AveragedResponse = Ssum_{index} / CountSum(index)$$

$$= Ssum_1 / CountSum(1)$$

$$= \begin{bmatrix} 1 \\ 4 \\ -3 \\ 9 \\ 4 \\ -1 \end{bmatrix} \div 2$$

-continued $$= \begin{bmatrix} 0.5 \\ 2 \\ -1.5 \\ 4.5 \\ 2 \\ -0.5 \end{bmatrix}$$

It should be understood that the above sample calculation is intended for illustrative purposes only, and in no way should such sample calculation be construed as limiting in any way on the scope of the present invention.

One application of the signal averaging technique discussed above with reference to FIGS. 3A-3D above is DPOAE testing. While the remainder of the application discusses DPOAE testing specifically, it should again be understood that the signal averaging technique of the present invention can be applied to any of the above-mentioned applications, or any other application that may benefit from signal averaging.

DPOAE testing analyzes the distortion product otoacoustic emissions (DPOAE) generated by the ear to determine middle ear function. More specifically, a DPOAE test device generates and emits two audible tones (i.e., test signals) at different frequencies into the ear canal of a subject. A healthy ear will produce, in response to the two audible tones, a response signal having a frequency that is a combination of the frequencies of the two audible tones. Thus if the two audible tones generated have frequencies of $f_1$ and $f_2$, respectively, a healthy subject's ear will emit a response signal having a frequency that is a combination of $f_1$ and $f_2$. The strongest response signal occurs at a frequency of $(2)(f_1)-f_2$, and is referred to as the distortion product.

In addition, DPOAE test devices also generally modify the frequencies of the audible tones transmitted into the ear canal over time during the course of the test. In response, a healthy subject's ear will emit a distortion product having a frequency that similarly changes over time during the course of the test. Generally speaking, the lack of distortion product otoacoustic emissions from the ear during the course of the test is an indication of possible hearing loss.

Otoacoustic emissions produced by a healthy ear are extremely small in magnitude, typically in the range from −10 dB SPL to +20 dB SPL. Any kind of background noise introduced into the ear canal or device, or improper placement of the test probe in the ear canal, may result in the inadvertent masking of the emissions (and thus the triggering of a false negative response), in an inaccurate measurement, or in an otherwise invalid result.

Figure 4:
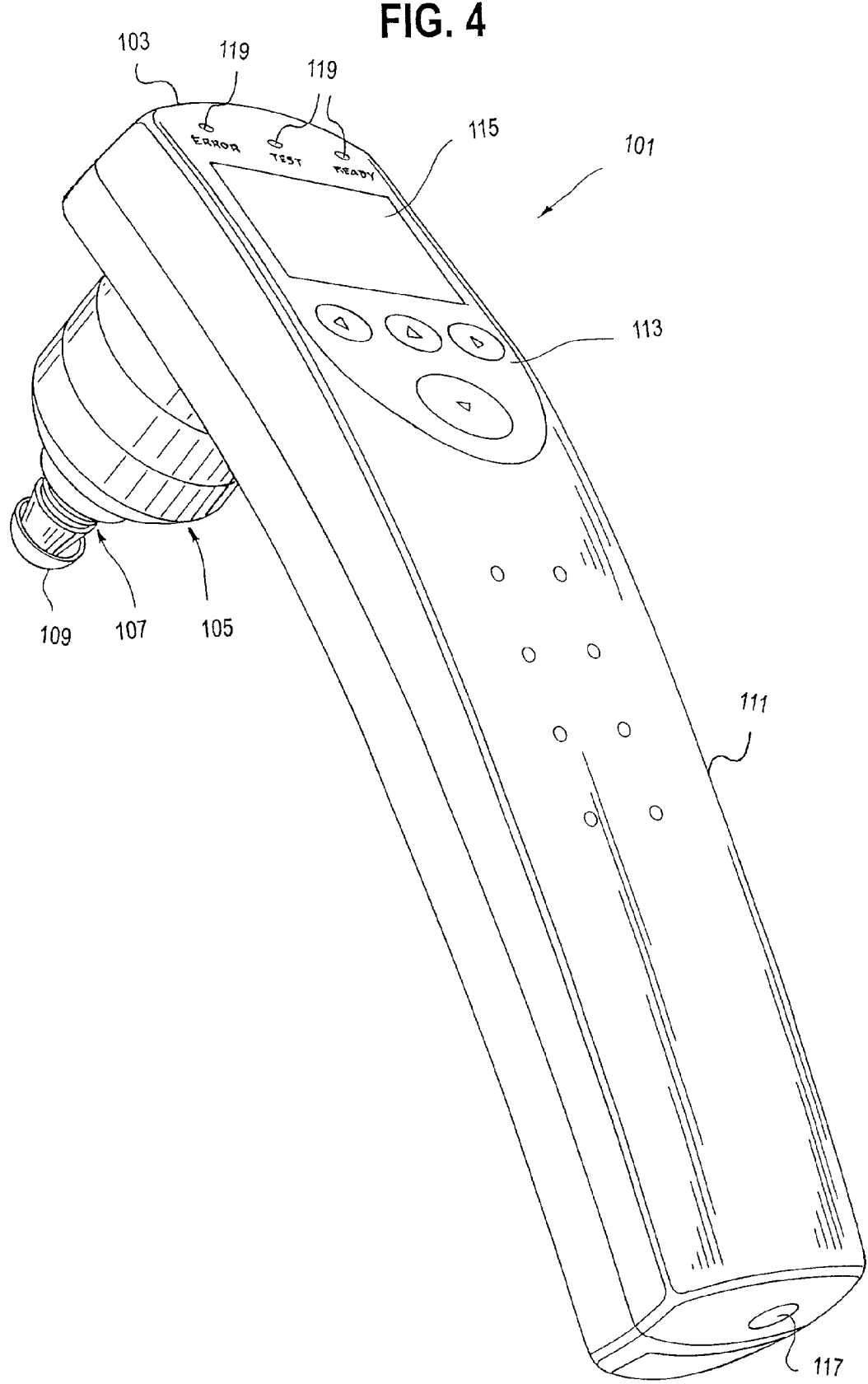
FIG. 4 illustrates an integrated, hand-held hearing test or screener device built in accordance with the present invention, which can be used for DPOAE testing.

FIG. 4 illustrates an integrated, hand-held hearing test or screener device built in accordance with the present invention, that may be used for DPOAE testing. The device 101 includes a housing or terminal portion 103, an isolation body or assembly 105 and a testing probe 107. The testing probe 107 includes an ear tip 109, which may be made of an elastic material, such as, for example, rubber. The testing probe 107 is integrated with the terminal portion 103 via the isolation body 105, which elastically couples or suspends the testing probe from the terminal portion 103. Additional detail regarding the isolation body 105 can be found in copending U.S. patent application Ser. No. 09/285,938 filed Apr. 2, 1999, which application is incorporated herein by reference in its entirety. While the testing probe 107 is illustrated in FIG. 4 as being integrated with the terminal portion 103, the testing probe 107 may be separate from the terminal portion 103 and connected to the terminal portion 103 via a cable (not shown). In addition, the device 101 itself may also be a stationary (i.e., not hand-held) device having a probe connected thereto via a cable, as is known in the art.

Referring again to FIG. 4, the terminal portion 103 includes a handle portion 111, a keyboard 113 and a display 115, which may be, for example, an LCD display. An operator grasps the handle portion 111, and manipulates the keyboard 113 with the operator's thumb (or forefinger). The operator may view the display 115 before, during and after the test. The terminal portion 103 also includes a data port (not shown) located on an underside of the handle portion 111. The data port enables the device 101 to be communicatively coupled to an external device, such as, for example, a personal computer, for download of test and related data or upload of programming or other information. The terminal portion 103 may also include additional visual indicators 119 (besides the display 115), such as, for example, light emitting diodes (LEDS), for indicating to the operator, for example, test status or the like. In FIG. 4, visual indicators 119 illustrate a "ready" status, a "test" status, and an "error" condition.

To perform a test, an operator grasps the handle portion 111 of the terminal portion 103 and moves the device 101 towards a test subject's ear (not shown). The operator then places the testing probe 107 into the subject's ear such that the ear tip 109 is seated within the subject's ear canal, and a test is initiated.

Figure 5:
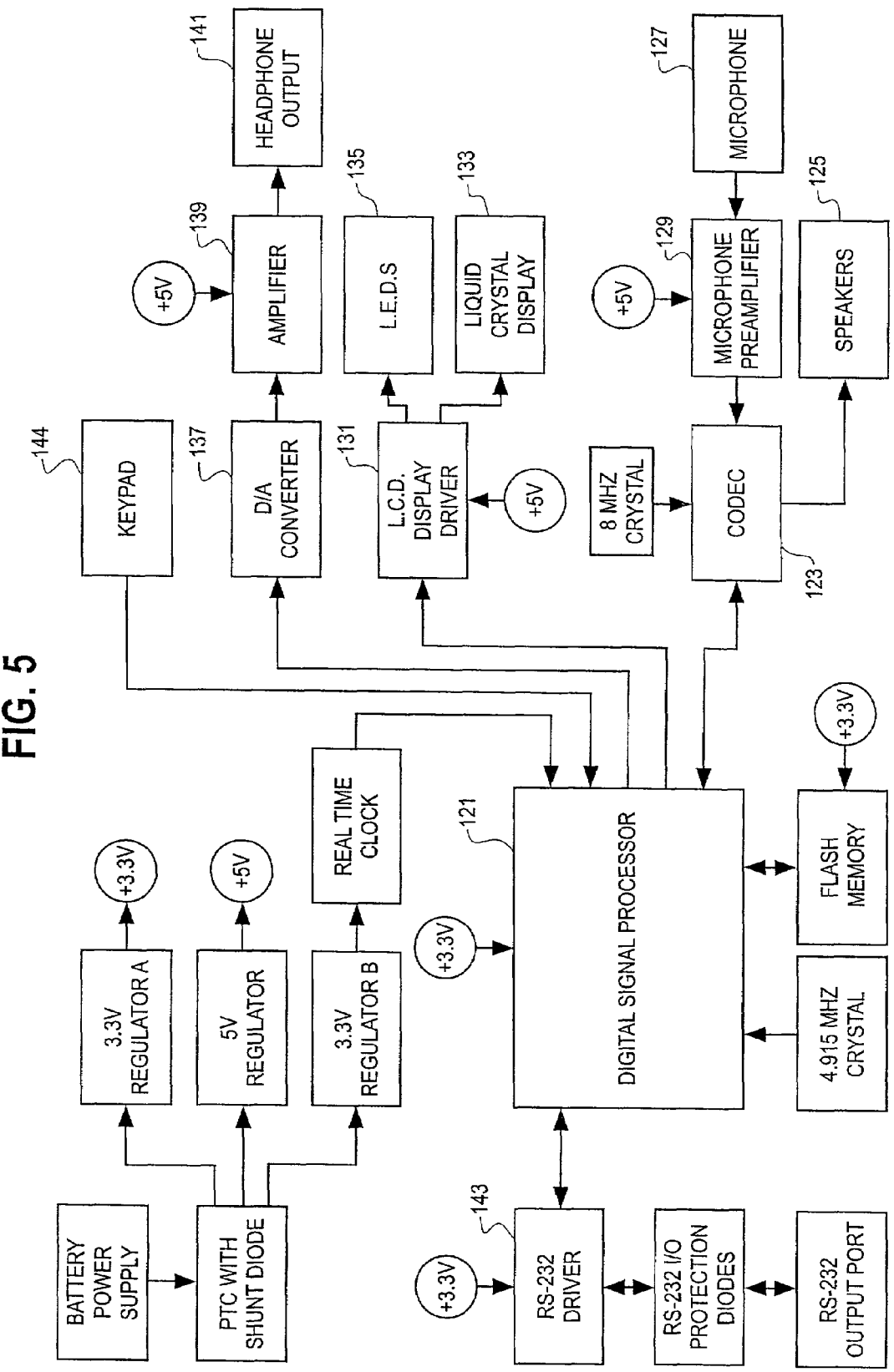
FIG. 5 is one embodiment of a block diagram of the hearing test or screener device of FIG. 4 built in accordance with the present invention.

FIG. 5 is a block diagram of a hearing test or screener device built in accordance with the present invention. The block diagram of FIG. 5 is one embodiment of the device 101 of FIG. 4, which may be used, for example, to perform DPOAE testing, as discussed above. Of course, other embodiments exist that may not incorporate all of the components shown in FIG. 5, or that may incorporate components that are different than, or components in addition to, those shown in FIG. 5.

The embodiment of FIG. 5 will now be discussed with reference to DPOAE testing. A digital signal processor (DSP) 121 generates digital signals representative of two audio tones of different frequencies and transmits the digital signals to a CODEC block 123 (i.e., an analog to digital and digital to analog converter), which converts the digital signals to electrical signals. The electrical signals are transmitted to an audio source 125, which may be, for example, located in the testing probe 107 of FIG. 4. The audio source 125 may comprise, for example, two audio speakers. The two audio speakers respectively transduce electrical signals into audible tones that are transmitted into the ear canal of a test subject. A microphone 127, which may, for example, be located in the testing probe 107 of FIG. 4, receives responsive audio signals from the ear of the test subject, and transduces the received audio signals into electrical signals representative of the received audio signals. The electrical signals are amplified by a microphone preamplifier 129, converted into digital signals by the block 123, and then communicated to the DSP 121. The DSP 121 then uses the signals to perform DPOAE analysis as is known in the art.

The DSP 121 also communicates output signals to the LCD Display Driver 131 which causes display of output data on the liquid crystal display 133 and/or indication of test status on visual indicators (e.g., LEDs) 135. In general, the output data comprises, for example, test results or the like. Output data, as such, may be displayed before, during and after the test. In fact, as discussed more completely below, the display may be used by an operator before the test to assist in properly placing the testing probe into the ear canal.

An operator may also use a headphone to further assist with proper placement of the testing probe in the ear. In one embodiment, the DSP 121 communicates digital signals (e.g., representative of the audio signals received from the ear) to a D/A converter 137 which converts the digital signals into electrical signals. The electrical signals are then amplified by the amplifier 139 and communicated to a headphone output 141. The headphone output 141, which may be, for example, headphone jack 117 shown in FIG. 4, is connected to a headphone assembly (not shown), which transduces the electrical signals into audio signals. Alternatively, the headphone output may be located adjacent the data port on the underside to the handle portion 111. With such a configuration, an operator may, for example, monitor the audio signals received from the ear to assist in the positioning and repositioning of the probe within the ear canal. Additional detail regarding audibly monitoring the condition in the ear can be found in copending U.S. patent application Ser. No. 08/971,520 filed Nov. 17, 1997, which application is incorporated herein by reference in its entirety.

In a further embodiment, the DSP 121 communicates status signals, to the headphone output 141, which signals can be audibly monitored by an operator via the headphones, to assist with the positioning of the probe within the ear canal.

The DSP 121 also downloads or uploads data via the data port by communication with RS-232 driver 143. In addition, keypad 144 enables an operator to enter data and/or commands into the device 101.

Figure 6A:
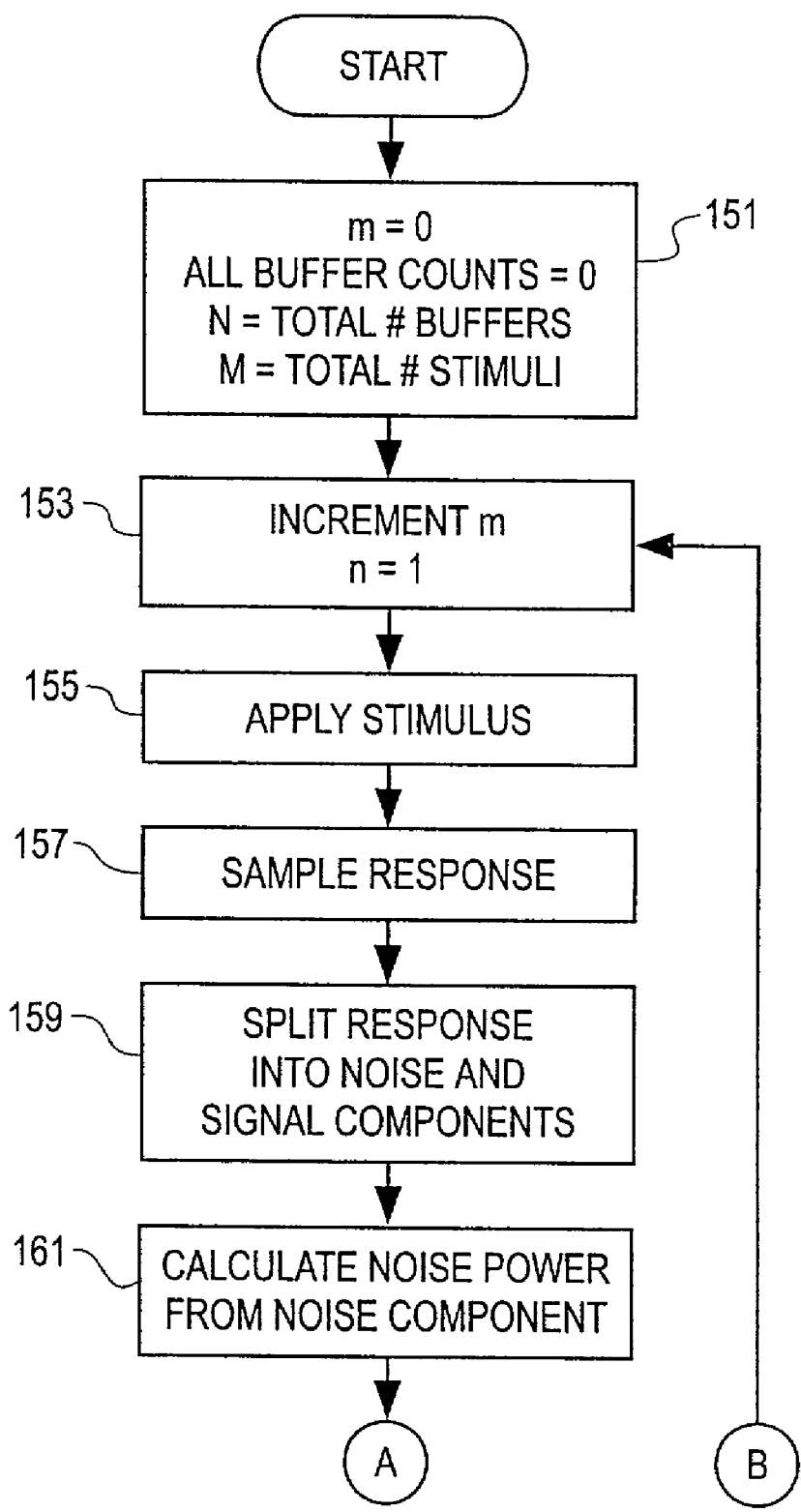
FIGS. 6A-6D are a flow diagram illustrating one embodiment of the artifact rejection method of the present invention that may be employed by the device/system of FIGS. 4 and 5.
Figure 6B:
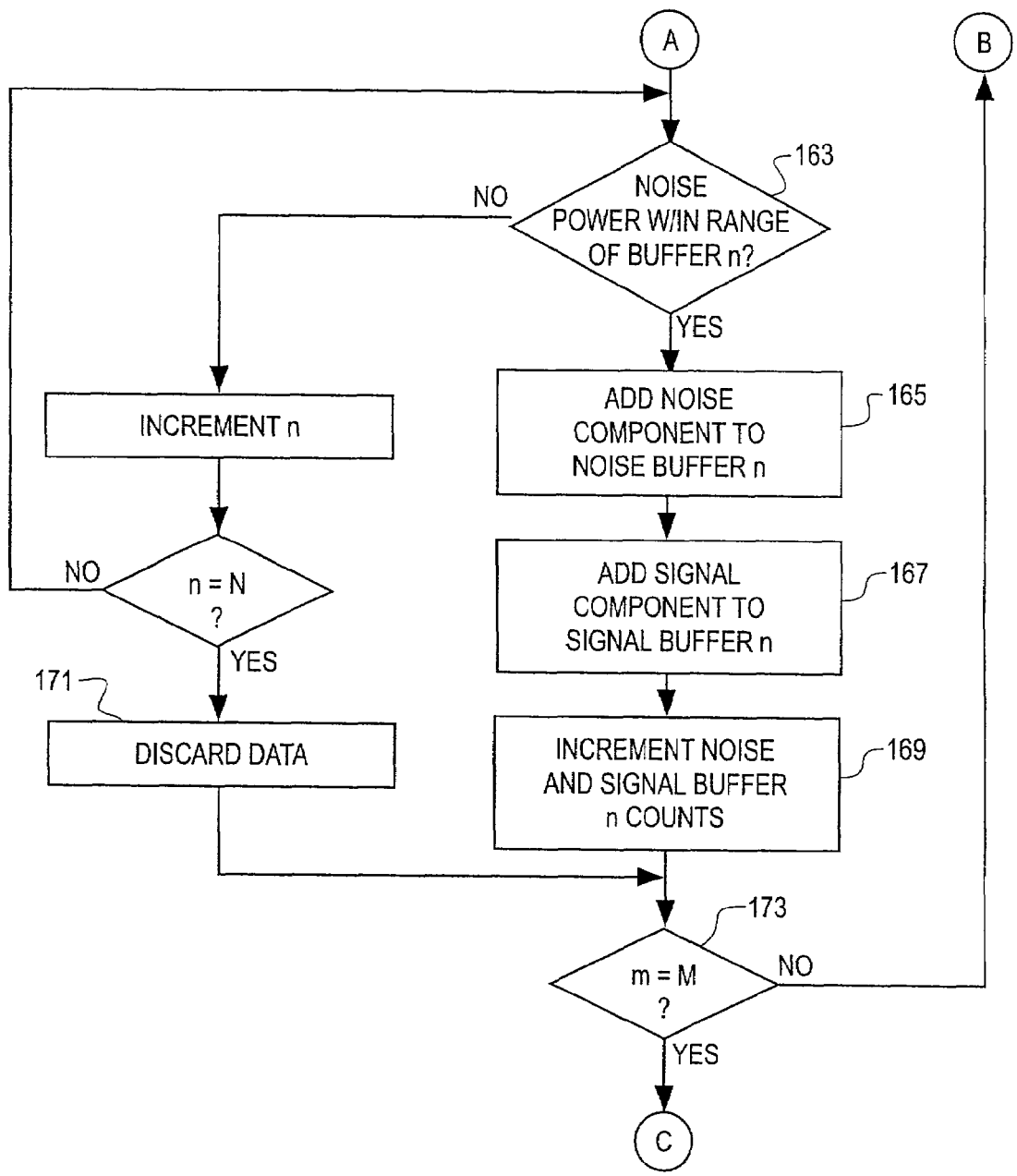

FIGS. 6A-6D are a flow diagram illustrating one embodiment of the artifact rejection method of present invention that may be employed using the device/system of FIGS. 4 and 5 in a DPOAE test. FIGS. 6A and 6B may be referred to as a data acquisition phase. The system is initialized by setting a counter variable m and all buffer counts to zero (block 151). The counter variable m is used in a loop to determine if the system has transmitted the total number of stimuli, represented by a variable M. The system then increments m and sets another counter variable n equal to 1 (block 153). The counter variable n is used in a second loop to determine which of a total number of buffers, represented by a variable N, corresponds to a response sampled that is responsive to a transmitted stimulus.

More specifically, the system applies a stimulus (block 155), and then samples the response to the stimulus (block 157). The system then splits the sampled response into separate noise and signal components (block 159). This may be achieved by, for example, taking a discrete Fourier transform ("DFT") of the response. Next, the system calculates the noise power from the noise component of the split response signal (block 161), and then determines whether the noise power is within a noise power range corresponding to a first buffer (block 163). If it is, the noise component is added to a first noise buffer (block 165), the signal component is added to a corresponding first signal buffer (block 167), and first noise and signal buffer counts are incremented (block 169). The system then loops back to transmit another stimulus.

If the noise power is not within range of the first noise buffer, the system loops to block 163 to determine whether the noise power is within a noise power range of a second buffer. Again, if it is, the noise component is added to a second noise buffer (block 165), the signal component is added to a corresponding second signal buffer (block 167), second noise and signal buffer counts are incremented (block 169), and the system loops to transmit another stimulus. If the noise power is not within range of the second noise buffer, the third noise buffer is tried, and so on. This loop is repeated for each of the total number of buffers N. If the noise power is not within range of any of the noise buffers, then the data is discarded (block 171). This whole process is repeated until the total number of stimuli M have been transmitted by the system (i.e., until m=M at block 173).

In other words, the system applies a stimulus, receives a response, splits the response into a noise component and a signal component, and then calculates the noise power of the noise component. Depending on the magnitude of the calculated noise power, the noise component of the response is placed in a noise buffer, and the signal component is placed in a corresponding signal buffer. This is repeated for a number of stimuli, and the system keeps track of the number of noise and signal components placed in each noise and signal buffer, respectively. Once the total number of stimuli have been transmitted by the system, data acquisition is complete.

Figure 6C:
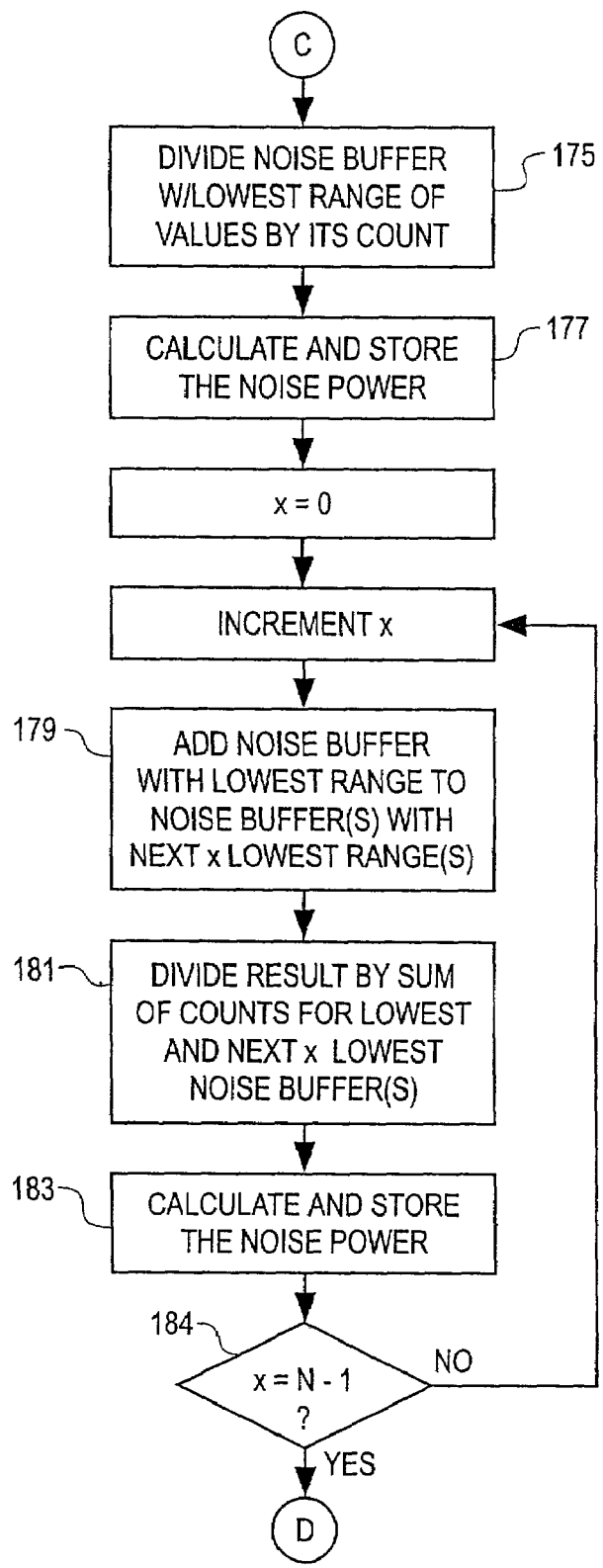
Figure 6D:
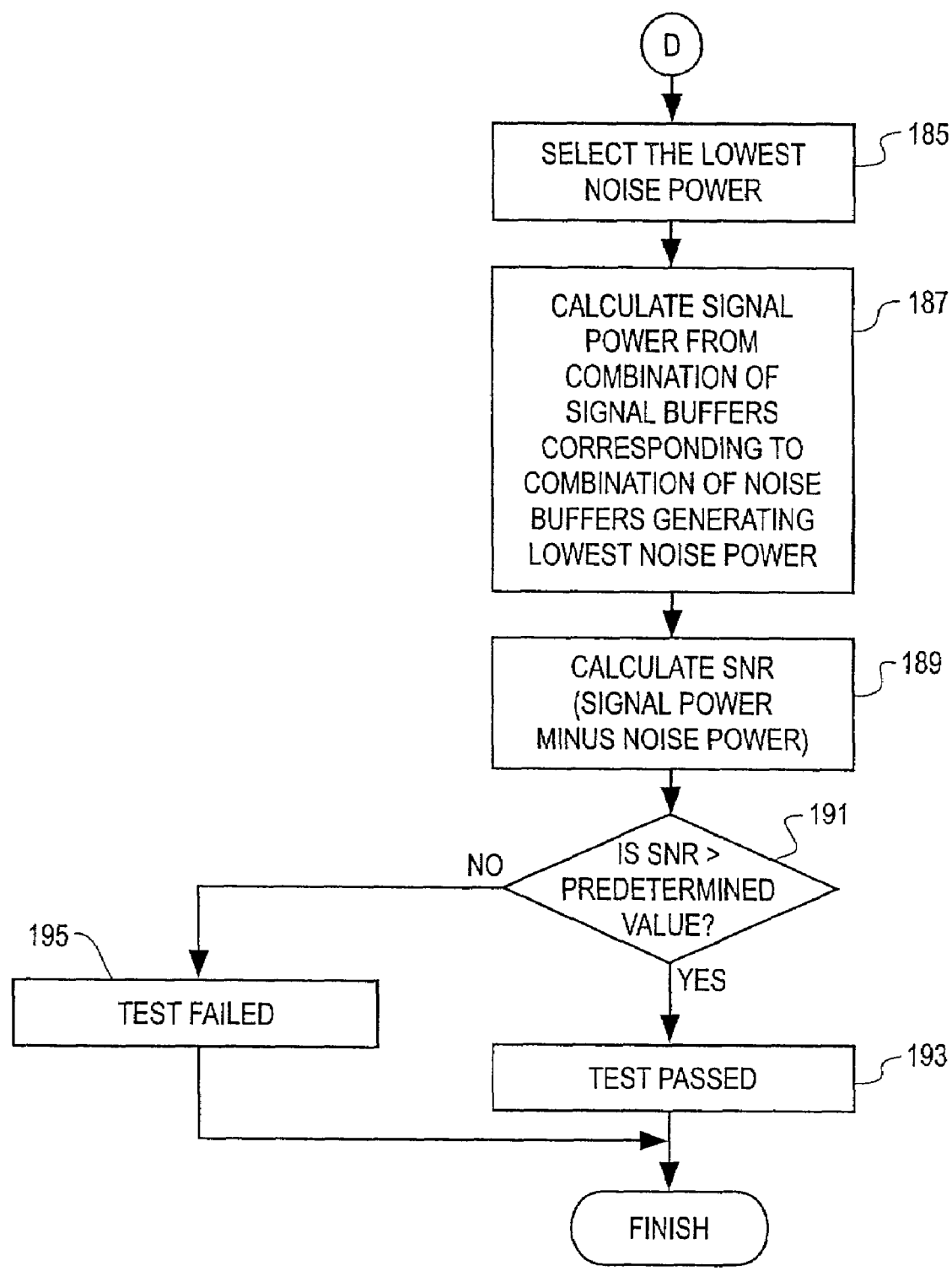

The system next advances to FIGS. 6C and 6D, which may be referred to as a data analysis phase. The system first divides the noise buffer with the lowest range of values by the number of noise components that were placed in that buffer (block 175). The result is then used to calculate the noise power, which is stored in a buffer (block 177).

The system next adds the noise buffer having the lowest range of values to the noise buffer having the next lowest range of values (block 179), and then divides the result by the total number of noise components that were placed in both of those buffers (block 181). This result is then used to calculate the noise power, which is stored in a buffer (block 183).

Similarly, the system next adds the buffer having the lowest range of values to the buffers having the next two lowest ranges of values (block 179) and then divides the result by the total number of noise components that were placed in those three buffers (block 181). This result is then used to calculate the noise power, which is likewise stored in a buffer (block 183).

This process is repeated for the total number of noise buffers (i.e., until x=N−1 at block 184), so that the system has N estimates of the noise power (i.e., noise floor). The system then selects the estimate (i.e., combination of noise buffers) with the lowest noise power (block 185). The selected combination of noise buffers represents the quietest portion of data. The system then calculates the signal power using the combination of signal buffers corresponding to the selected combination of noise buffers (block 187).

At this point, the system has a noise power value and a signal power value, and uses those values to calculate the signal to noise ratio ("SNR") from signal power minus noise power (block 189). The system then tests to determine whether the SNR is greater than some predetermined value (block 191). If it is, then the test is considered a pass (block 193). If it is not, then the test is considered a fail (block 195).

FIGS. 7A-7F are a more detailed flow diagram of one embodiment of the artifact rejection method that may be employed by the device/system of FIGS. 4 and 5 in a DPOAE test. The following are variable definitions used in conjunction with FIGS. 7A-7F:

Stimulus = Output to system (vector − size N)
$X(n)$ = current response from system
  - note that the complete response X need not be saved
XF = DFT of X (complex vector − size K)
table = frequency index values for DFT (vector − size K)
  - Fbin=SampleRate/N ~ e.g., 31 Hz
  table(1) = round (F1/Fbin)   stimulus frequency
  table(2) = round (F2/Fbin)   stimulus frequency
  table(3) = (2*F1−F2)/Fbin    distortion frequency
  table(4) = table(3)−2        noise floor frequency -continued

```
        table(5) = table(3)-1
        table(6) = table(3)+1
        table(7) = table(3)+2
S = DFT sum buffers (complex matrix - size K by M)
Count = buffer count (vector - size M)
T = threshold values (vector - size M)
        Constant = frequency depended starting value
        T(1) Constant
        T(2) = 2 * Constant
        T(3) = 4 * Constant
        T(4) = 8 * Constant
        T(5) = 16 * Constant
        T(6) = 32 * Constant
        T(7) = 64 * Constant
        T(8) = 128 * Constant
Ssum = cumulative sum buffer (complex vector - size K)
Countsum = cumulative sum count (vector - size M)
NF = noise floor estimate based on Ssum (vector –size M)
W = penalty weighting function (vector –size M)
        W(1) to W(7)    = 2
        W(8)            = 1
AveragedResponse = final signal estimate (complex vector - size K)
K = number of DFT points (e.g., 7)
M = number of sum buffers (e.g., 8)
N = stimulus and DFT length (e.g., 1024)
blocksmax = total number of stimulus to apply to system (e.g., 64)
nf = noise floor of the current noise component
```

The system is initialized by setting the variables S, blocks and Count equal to zero (block 201). In addition, a loop variable n is set to 1, and XF, which represents a discrete Fourier transform (DFT) of a response, is set to zero (block 203). Next, a Stimulus(n), which represents a single point in a total stimulus, is transmitted by the system (block 205), and a response point X(n) is received by the system in response to the Stimulus(n) point (block 207).

Once a response point X(n) is received, the system enters a loop to perform a DFT of that response point for a plurality of different frequencies. More specifically, the system first sets the internal loop variable k equal to 1 (block 209), and then accesses a look up table in memory to find a Fi value, table(k), corresponding to a first frequency (i.e., table(1)) (block 211). The system then takes the DFT of the response point X(n) using the table(1) value obtained from the look up table and the formula set forth in block 213. The system then loops to find a Fi value, table(k), corresponding to a second frequency (i.e., table(2)) (block 211). The system then takes the DFT of the second response point using the table(2) value and the formula in block 213. This loop is repeated until the total number of frequencies have been utilized (i.e., when k>K at block 215).

In other words, the system takes the DFT of one point of the response at K different frequencies, stores the values, and adds the K different values generated. In one embodiment, K may comprise 7 different frequencies, and thus Fi (i.e., table) comprises 7 different values in memory. As mentioned above, table represents a frequency index value for the DFT. The table values may be predetermined using the table equations set forth above and several values for F1, F2 and Fbin.

More particularly, in one embodiment, F2 is set to 2000 Hz, the DFT length N is set to 1024 points, and the sample rate is set to 31250 samples per second. In addition, F1 may be established using a ratio relative to F2. In this embodiment, a DFT bin size, Fbin, may be calculated as follows:

$$Fbin = SampleRate/N$$
$$= 31250/1024$$
$$\sim 31 \text{ Hz}$$

Table(2) can then be calculated as follows:

$$table(2) = round(F2/Fbin)$$
$$= round(65.536)$$
$$= 66$$

If the ratio of table(2) to table(1) is 1.2, for example, then table(1) may be calculated as follows:

$$table(1) = round(table(2)/ratio)$$
$$table(1) = round(66/1.2)$$
$$= 55$$

Alternatively, table(1) may be calculated using the following equation (set forth above):

$$table(1) = round(F1/Fbin)$$

In any case, the remainder of the table values, assuming K=7, are calculated using the equations set forth above as follows:

$$table(3) = 2(table(1)) - table(2)$$
$$= 2(55) - 66$$
$$= 44$$

$$table(4) = table(3) - 2$$
$$= 44 - 2$$
$$= 42$$

$$table(5) = table(3) - 1$$
$$= 44 - 1$$
$$= 43$$

$$table(6) = table(3) + 1$$
$$= 44 + 1$$
$$= 45$$

$$table(7) = table(3) + 2$$
$$= 44 + 2$$
$$= 46$$

Thus, at a stimulus frequency F2 of 2000 Hz, the following table vector results:

table=[55, 66, 44, 42, 43, 45, 46]

If stimulus frequencies of 3000 and 4000 Hz are used for F2, and if all other values are the same, the following two table vectors result, respectively:

table = [82, 98, 66, 64, 65, 67, 68]

table = [109, 131, 87, 85, 86, 88, 89]

As mentioned above, these table vectors are stored in a look-up table in memory.

Once the DFT is taken of the first point in the response at K different frequencies (block 215), the system loops to block 205 to transmit another point, Stimulus(n), in the total stimulus. The whole process is repeated until all points in the total stimulus have been transmitted, and the DFT of all the response points has been taken at K different frequencies (i.e., when n>N at block 217).

At this point, a single complete stimulus has been transmitted, and a corresponding DFT of the response has been collected, each having a length of N (i.e., N points). As mentioned above, N may be 1024 points. The system then calculates the noise floor using the formula set forth in block 219. As can be seen, this formula uses the DFT values of the response (i.e., XF) corresponding to the $4^{th}$, $5^{th}$, $6^{th}$ and $7^{th}$ frequencies, since these frequencies relate to the noise portion of the response.

Once the noise floor is calculated, the system determines whether the noise floor value is less than a lowest threshold value T(1) of a vector T (block 221). As mentioned above, the vector T has values that are monotonically increasing, and T(1) is a predetermined constant dependent on the value of F2 as follows:

| F2 (Hz) | T(1) (dB SPL) |
|---|---|
| F2 ≦ 1500 | −7 |
| 1500 < F2 ≦ 2000 | −9 |
| 2000 < F2 ≦ 2300 | −10 |
| 2300 < F2 ≦ 2600 | −11 |
| 2600 < F2 ≦ 3000 | −13 |
| 3000 < F2 ≦ 3500 | −14 |
| 3500 < F2 | −15 |

The remainder of the T vector, which has a length M (i.e., equal to the number of buffers, e.g., 8), can then be calculated from T(1), using the equations set forth above. In this embodiment the T values represent the noise floor level in the 1 Hz band, with a conversion value to correlate them with the values used to calculate the noise floor, which are in the 31 Hz band.

Figure 7A:
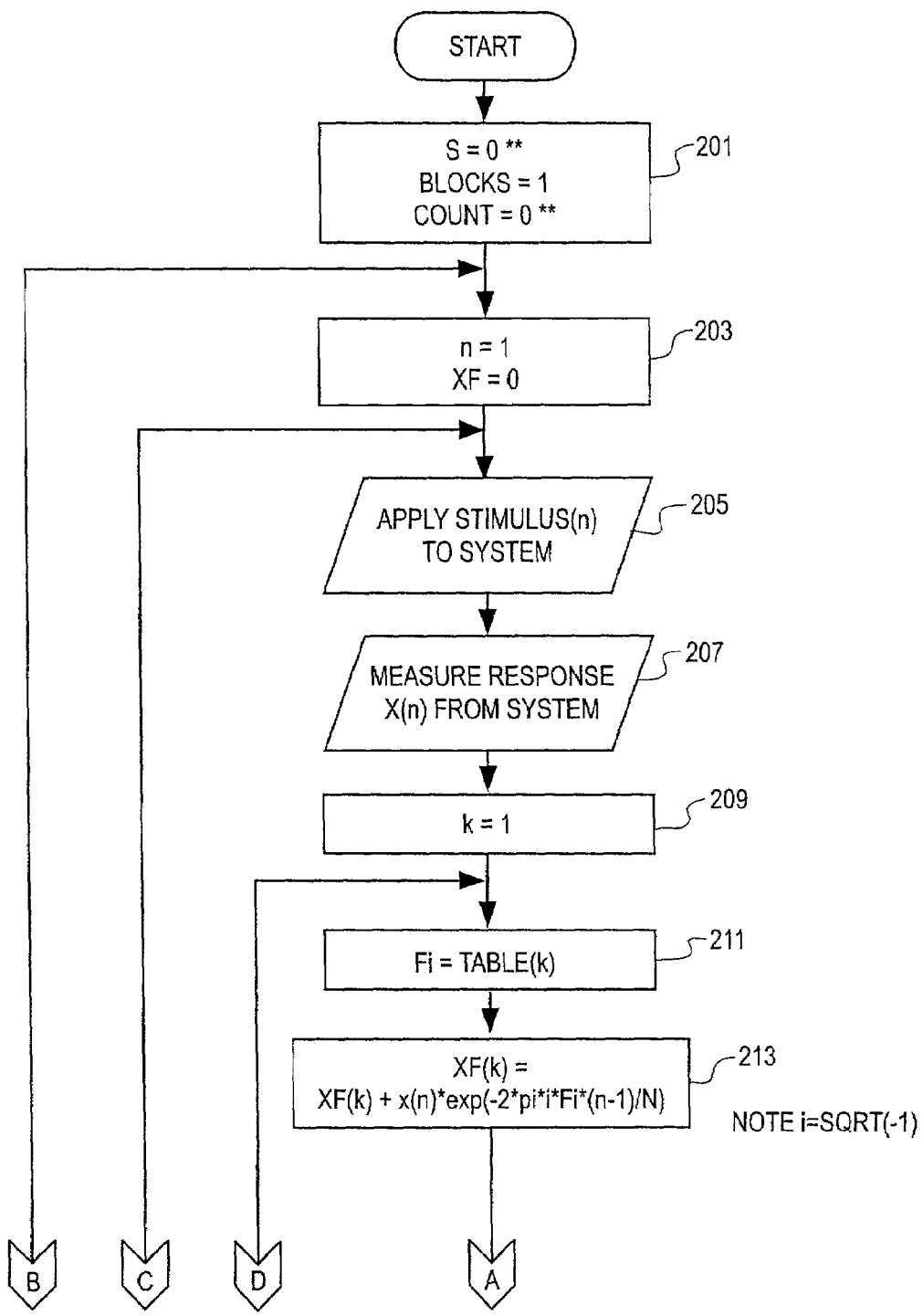
FIGS. 7A-7F are a more detailed flow diagram of one embodiment of the artifact rejection method that may be employed by the device/system of FIGS. 4 and 5 in a DPOAE test.
Figure 7B:
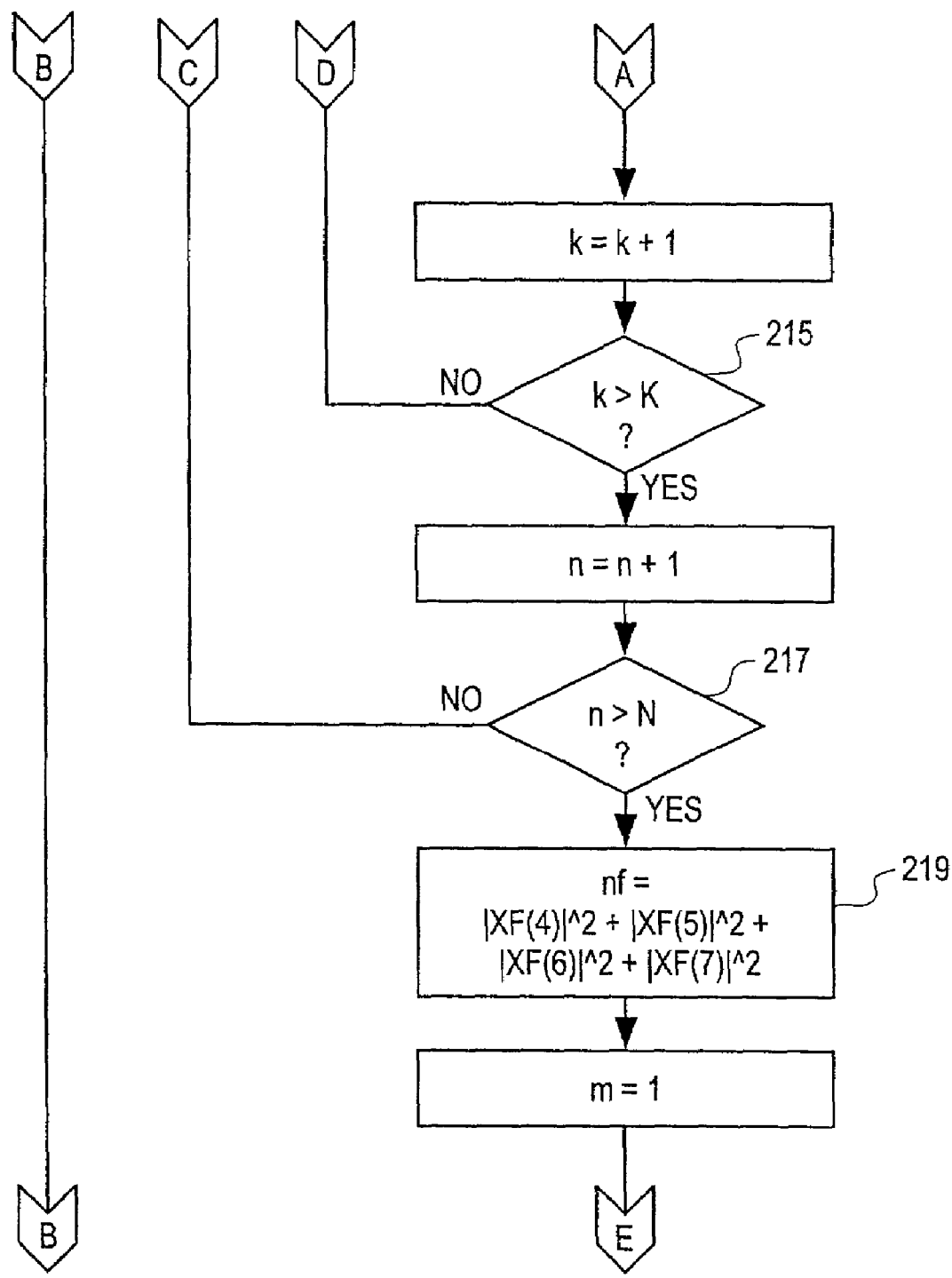
Figure 7C:
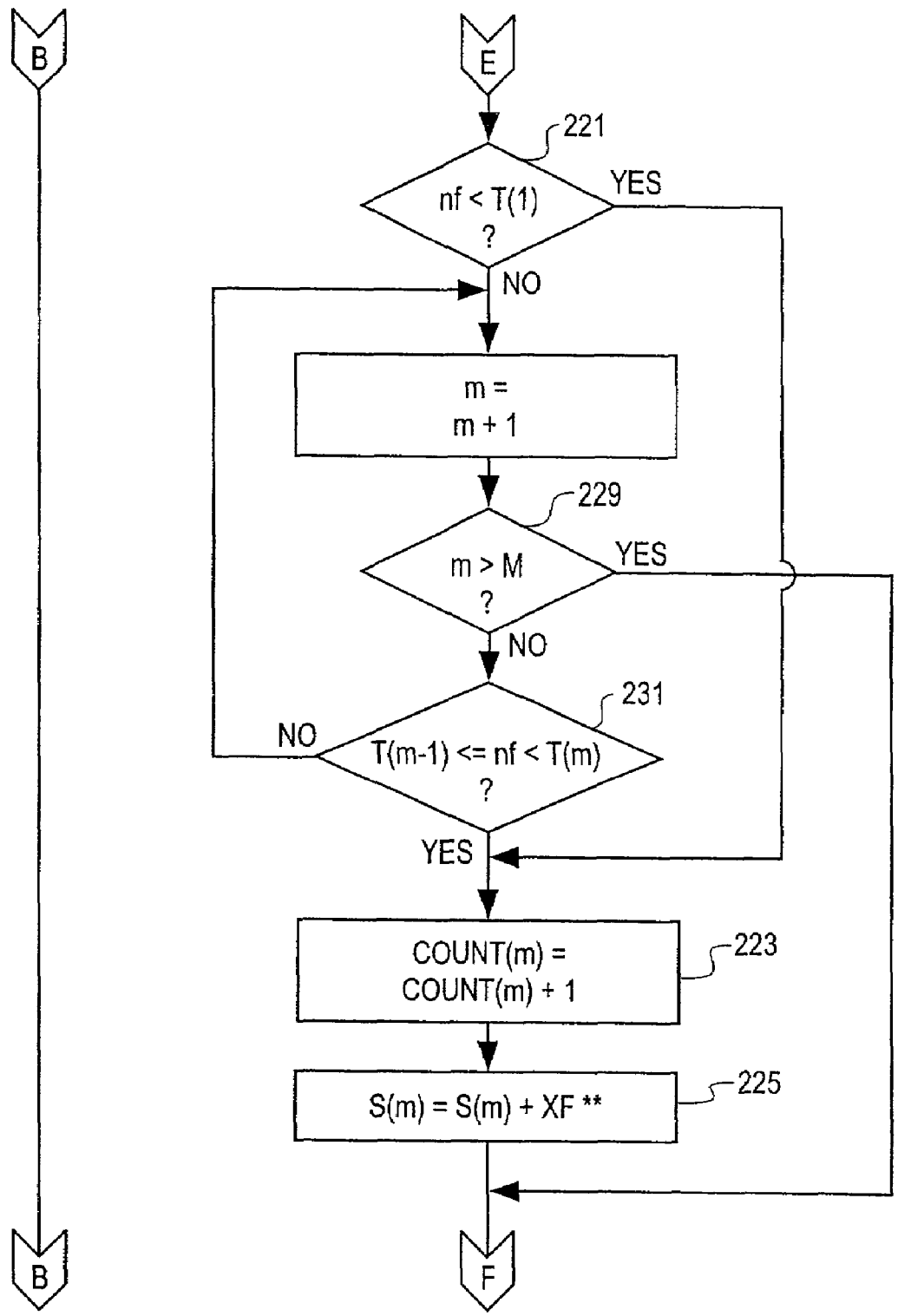
Figure 7D:
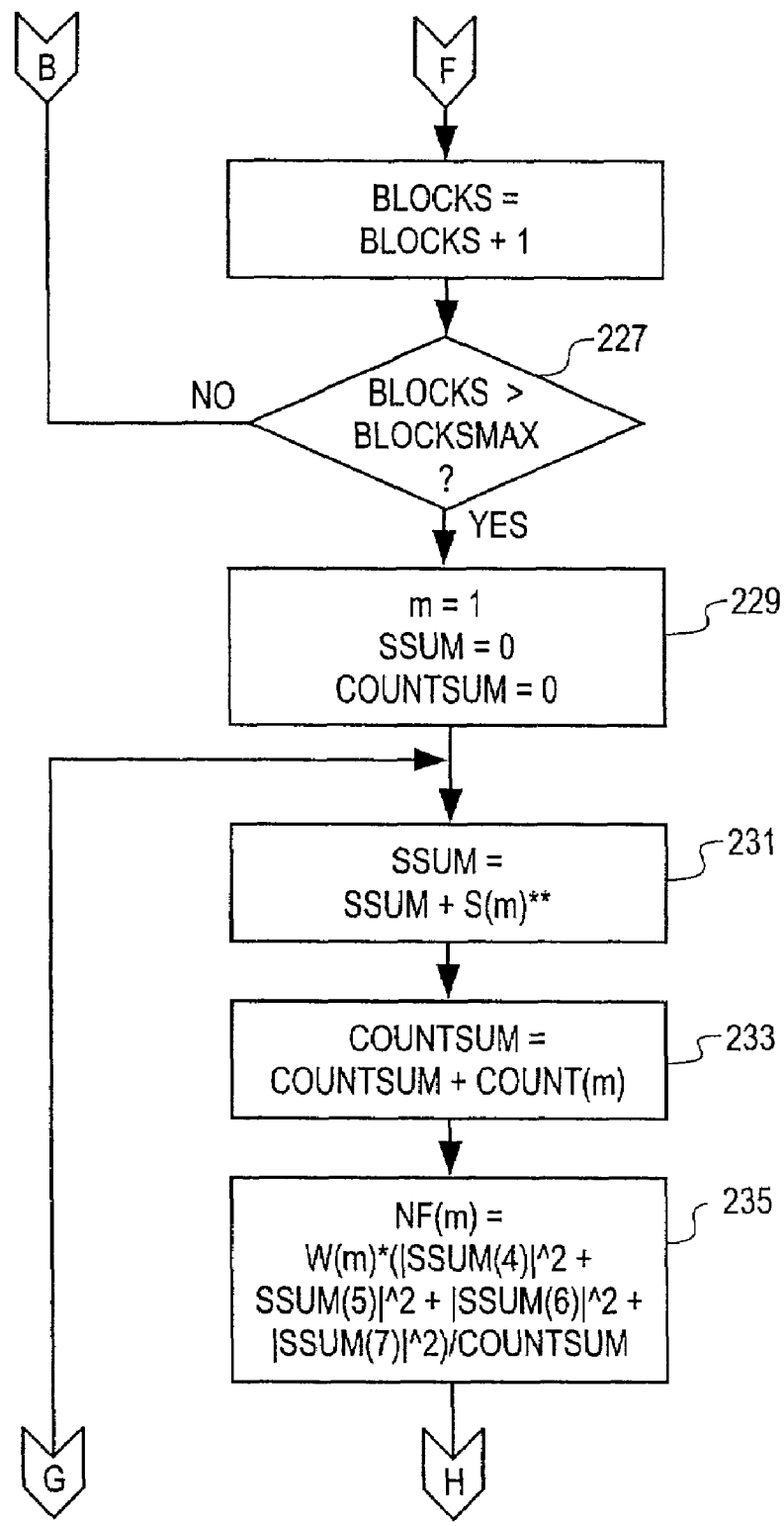
Figure 7E:
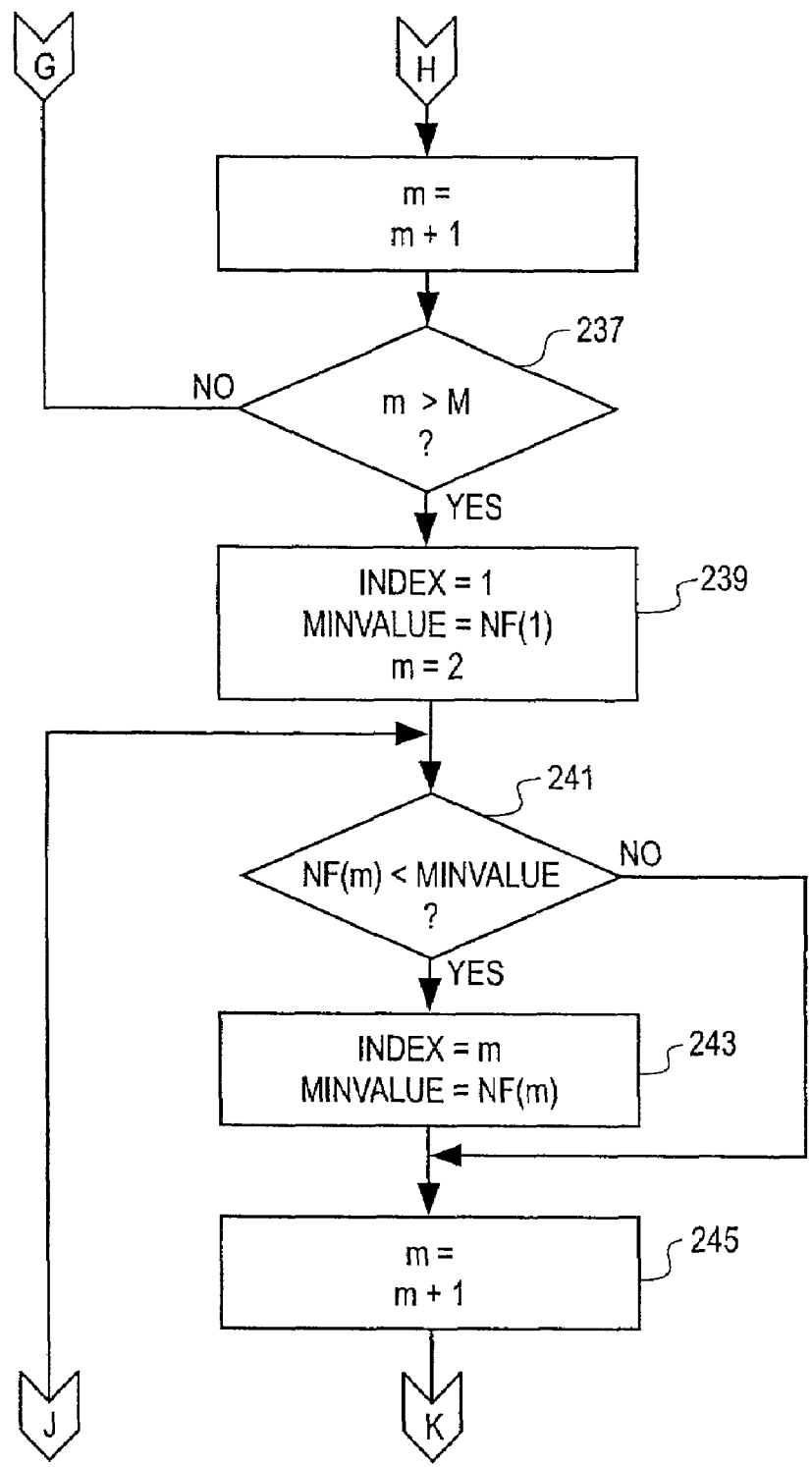
Figure 7F:
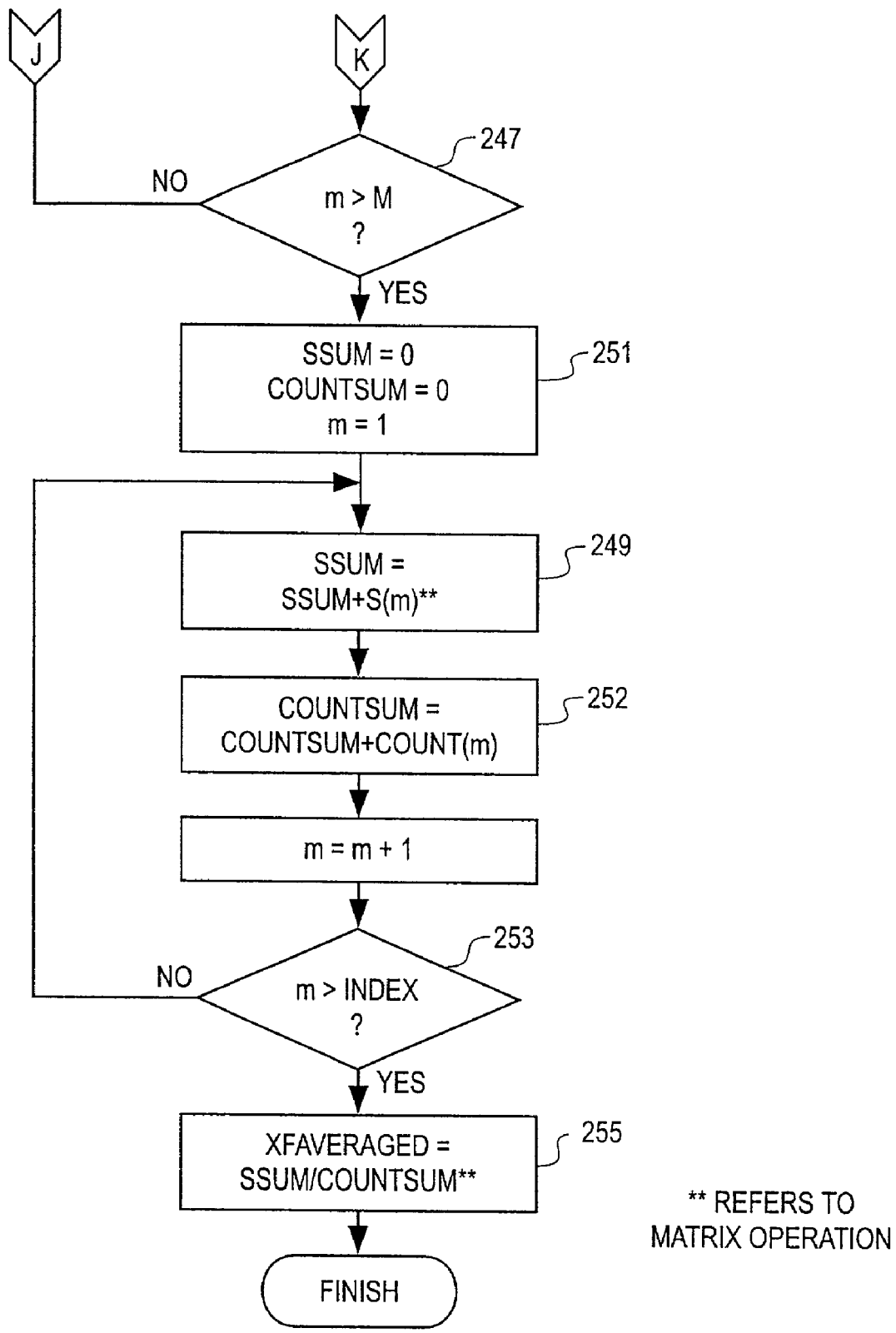

Referring again to block 221 of FIG. 7C, if the noise floor is less than T(1), the first position in the Count vector is incremented (block 223), and the DFT of the response (XF) is added to the first DFT sum buffer column (block 225). The system then determines whether all stimuli have been transmitted by the system (block 227), and, if not, loops back to apply another stimulus.

If the noise floor is not less than T(1), the system enters a loop, limited by the number of buffers M (block 229) to determine whether the noise floor falls between two successive values in T (block 231). In other words, the system loops to determine in which buffer (i.e., column in matrix S) the noise floor belongs. If the noise floor falls within an appropriate range of T, the Count vector is incremented (block 223), keeping track of how many times each respective noise floor falls within that range, and the DFT of the response (XF) is added to the associated DFT sum buffer column (block 225).

If the noise floor does not fall within an appropriate range of T, the DFT of the response is discarded.

In any event, the system continues the above process until the total number of stimuli have been transmitted by the system (block 227). When the total number of stimuli have been transmitted (i.e., when blocks>blocksmax), data acquisition is complete. At this point, the DFT's of the responses have been sorted and reside in appropriate buffers.

Data analysis or processing is next, and is initialized by setting the loop variable m equal to 1, cumulative sum buffers (Ssum) matrix to zero, and the cumulative sum count (Count-Sum) vector to zero (block 229). The system next enters a loop to generate M calculations of the noise floor estimate based on the DFT sum buffers. Generally, this is achieved by generating a cumulative sum matrix (Ssum) and a cumulative sum count vector (CountSum) (blocks 231 and 233, respectively), using those calculations along with a penalty weighting function to calculate the noise floor estimate NF.

More specifically, in a first loop, $Ssum_1$ is determined to be equal to $S_1$, CountSum(1) is determined to be equal to Count (1), and NF(1) is calculated using the formula in block 235. As can be seen, only the $4^{th}$, $5^{th}$, $6^{th}$ and $7^{th}$ frequencies are used in the Ssum calculation in the formula. Again, these frequencies relate to the noise portion of the response. Also as can be seen, a penalty weighting function W is used. Again, the penalty weighting function is designed to force the system to accept more data than it otherwise would under non-weighted conditions. In one embodiment, the W vector is as set forth above.

As mentioned above, $S_1$ represents all the DFT components of the responses (i.e., noise signals) having a noise floor calculation determined to be less than T(1), and Count(1) equals the total number of such components.

Next, in a second loop, $Ssum_2$ is calculated as $Ssum_1 + S_2$, CountSum(2) is calculated as CountSum(1)+Count(2), and the noise floor estimate is calculated using the formula set forth in block 235. As mentioned above, $S_2$ represents all the DFT components with noise floors that are not less than T(1) but are less than T(2).

In a third loop, $Ssum_3$ is calculated as $Ssum_2 + S_3$, CountSum(3) is calculated as CountSum(2)+Count(3), and NF(3) is calculated using the formula set forth in block 235. As mentioned above, $S_3$ represents all the DFT components with noise floors that are not less than T(2), but are less than T(3).

The above calculations are repeated until the loop variable m is greater than M (block 237), indicating that all buffers have been considered and M noise floor estimates have resulted (NF vector).

The system next enters a loop to determine which NF value is the smallest. The loop is initialized by setting an index variable equal to 1, a minvalue variable equal to the first noise floor estimate NF(1), and a loop variable m equal to 2 (block 239). Next, NF(2) is compared to minvalue (i.e., NF(1)) (block 241). If NF(2) is not lower than NF(1), then the index remains at 1 and minvalue remains as NF(1). If NF(2) is lower than NF(1), the index is set at 2 and minvalue is set to equal NF(2) (block 243). In either case, the loop variable m is incremented (block 245), and the loop repeats until all M buffers have been considered (block 247).

As mentioned above, NF(1) is compared to NF(2), and the smaller is chosen. The smaller of NF(1) and NF(2) is then compared to NF(3) and the smaller is chosen. The smallest of NF(1), NF(2) and NF(3) is then compared to NF(4), and the smaller is chosen, and so on for all M noise floor (NF) buffers. Each time a lower NF value is found, the index, which is basically a pointer to a NF vector position, and the minvalue are modified. When all estimates have been considered, the final index indicates which position contains the lowest NF value (i.e., minvalue).

Once the index is determined, the system enters a loop to generate a new Ssum matrix and a new Ssum vector. The loop is initialized by setting Ssum and CountSum equal to zero, and the loop variable m equal to one (block 251). Similarly as explained above, the system generates Ssum and CountSum (blocks 249 and 252, respectively) using only that combination of buffers that gives the lowest noise floor estimate. The loop ends when the loop variable M is greater than the index (block 253). In other words, all buffers that have numbers lower than, and including, the index, are used to generate Ssum and CountSum. For example, if the index is five, meaning NF(5) is the lowest noise floor estimate, then buffers 1-5 are used to generate Ssum and CountSum.

Once Ssum and CountSum are generated, the final averaged response, XFaveraged, is calculated by dividing Ssum by CountSum (block 255). XFaveraged includes both noise and signal components, but they are separated. From this the SNR may be calculated.

In one embodiment, the method of FIGS. 7A-7E may be used by the device/system of FIGS. 4 and 5 in a DPOAE test. For example, the system may employ the method of FIGS. 7A-7E to obtain the signal and noise components for three sets of stimuli. Each stimulus may consist of having the following frequencies and pressures:

| Stimulus No. | F1    | P1 | F2   | P2 |
|--------------|-------|----|------|----|
| 1            | F2/1.2| 65 | 2000 | 55 |
| 2            | F2/1.2| 65 | 3000 | 55 |
| 3            | F2/1.2| 65 | 4000 | 55 |

After obtaining the signal and noise components for each set of stimuli, the system calculates the SNR as follows:

| Stimulus No. | Signal (dB SPL) | Noise (dB SPL) | SNR (dB)       |
|--------------|-----------------|----------------|----------------|
| 1            | S1              | N1             | SNR1 = S1−N1   |
| 2            | S2              | N2             | SNR2 = S2−N2   |
| 3            | S3              | N3             | SNR3 = S3−N3   |

In one embodiment, if all three of the SNR values (i.e., SNR1 SNR3) are greater than a predetermined amount (e.g., 5 dB), the DPOAE test is considered a pass. If not, the text is considered a fail.

Many modifications and variations of the present invention are possible in light of the above teachings. Thus, it is to be understood that, within the scope of the appended claims, the invention may be otherwise than as described hereinabove.

We claim:

1. A method of artifact rejection comprising:
   (a) transmitting a stimulus;
   (b) receiving a response to the stimulus;
   (c) splitting the response into a noise component and a signal component;
   (d) calculating a noise power from the noise component;
   (e) based on the calculated noise power, storing the noise component in one of a plurality of noise buffers and the signal component in a corresponding one of a plurality of signal buffers;
   (f) repeating steps (a) through (e);
   (g) selecting a combination of the plurality of noise buffers to which noise components were stored in step (e), the selected combination of the plurality of noise buffers having a lowest noise power; and
   (h) calculating a signal power from a combination of signal buffers corresponding to the selected combination of noise buffers.

2. The method of claim 1 further comprising counting the number of noise and signal components stored in each of the plurality of noise buffers and signal buffers, respectively.

3. The method of claim 1 further comprising:
   calculating a signal power to noise ratio from the calculated signal and the lowest noise power; and
   comparing the calculated signal to noise ratio to a predetermined value.

4. The method of claim 3 further comprising performing a function if the calculated signal to noise ratio is greater than the predetermined value.

5. The method of claim 3 further comprising performing a function if the calculated signal to noise ratio is less than the predetermined value.

6. The method of claim 1 wherein each stimulus comprises a plurality of points.

7. The method of claim 6 wherein each stimulus comprises 1024 points.

8. The method of claim 1 wherein each of the plurality of noise and signal buffers comprise eight buffers.

9. The method of claim 1 wherein the method is employed in one of a DPOAE test, a TEOAE test, a BAER test, an ultrasound operation, an MRI operation, a RADAR operation, a GPS operation, an EEG operation, an EKG operation, or a communications operation.

10. The method of claim 1 wherein splitting the response into a noise component and a signal component comprises taking the discrete Fourier transform of the response.

11. The method of claim 10 wherein seven different frequencies are employed.

12. The method of claim 1 further comprising discarding the response if the noise power of the noise component does not fit within an acceptable range of the plurality of noise buffers.

13. A method of artifact rejection comprising:
   (a) transmitting a stimulus;
   (b) receiving a response to the stimulus;
   (c) calculating a noise power from the response;
   (d) based on the calculated noise power, storing the response in one of a plurality of buffers;
   (e) repeating steps (a) through (d);
   (f) selecting a combination of the plurality of buffers to which responses were stored in step (d), the selected combination of the plurality of buffers having a lowest noise power; and
   (g) calculating a signal power based on the selected combination of buffers.

14. The method of claim 13 further comprising counting the number of responses stored in each of the plurality of buffers.

15. The method of claim 13 further comprising:
   calculating a signal power to noise ratio from the calculated signal and the lowest noise power; and
   comparing the calculated signal to noise ratio to a predetermined value.

16. The method of claim 15 further comprising performing a function if the calculated signal to noise ratio is greater than the predetermined value.

17. The method of claim 15 further comprising performing a function if the calculated signal to noise ratio is less than the predetermined value.

18. The method of claim 13 further comprising discarding the response if its calculated noise power does not fall within one of a plurality of acceptable noise power ranges corresponding to respective ones of the plurality of buffers.

* * * * *